(12) United States Patent
Han et al.

(10) Patent No.: US 12,271,585 B2
(45) Date of Patent: Apr. 8, 2025

(54) GRAPHICAL USER INTERFACE FOR A FLOW THERAPY APPARATUS

(71) Applicant: Fisher & Paykel Healthcare Limited, Auckland (NZ)

(72) Inventors: Jae Chul Han, Auckland (NZ); Hamish Chan, Auckland (NZ); Michael Jesse Robertson, Auckland (NZ); Kevin Peter O'Donnell, Auckland (NZ); Christopher Malcolm Crone, Auckland (NZ); Robert Stuart Kirton, Auckland (NZ); James Alexander Michael Revie, Auckland (NZ); Jose Ricardo Joven Catapang, Auckland (NZ); Jonathan Jaeheuk Lee, Auckland (NZ); Hayden Ross Purdy, Auckland (NZ); Anton Kim Gulley, Auckland (NZ); Christopher Harding Campbell, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/194,593

(22) Filed: Mar. 31, 2023

(65) Prior Publication Data

US 2023/0350557 A1  Nov. 2, 2023

Related U.S. Application Data

(63) Continuation of application No. 16/768,606, filed as application No. PCT/NZ2018/050174 on Dec. 7, 2018, now Pat. No. 11,789,598.

(60) Provisional application No. 62/596,726, filed on Dec. 8, 2017.

(51) Int. Cl.
| | |
|---|---|
| G06F 3/048 | (2013.01) |
| A61B 5/00 | (2006.01) |
| A61B 5/1455 | (2006.01) |
| A61M 16/06 | (2006.01) |

(Continued)

(52) U.S. Cl.
CPC ...... *G06F 3/04847* (2013.01); *A61B 5/14551* (2013.01); *A61B 5/7425* (2013.01);
(Continued)

(58) Field of Classification Search
CPC ............ G06F 3/04847; G06F 3/04817; A61B 5/14551; A61B 5/7425; A61B 5/746;
(Continued)

(56) References Cited

U.S. PATENT DOCUMENTS

| | | | |
|---|---|---|---|
| 5,881,723 A | 3/1999 | Wallace et al. | |
| 6,369,838 B1 | 4/2002 | Wallace et al. | |

(Continued)

FOREIGN PATENT DOCUMENTS

| | | |
|---|---|---|
| JP | 2004524879 A | 8/2004 |
| WO | WO 01/032069 | 5/2001 |

(Continued)

OTHER PUBLICATIONS

International Search Report and Written Opinion of the International Searching Authority for International Application No. PCT/NZ2018/050174, mailed on May 1, 2019, in 19 pages.

(Continued)

*Primary Examiner* — David E Choi
(74) *Attorney, Agent, or Firm* — Knobbe, Martens, Olson & Bear, LLP

(57) ABSTRACT

The present disclosure provides to graphical user interfaces for controlling a flow therapy apparatus. The graphical user interface can provide a display of flow therapy treatment information and indicators of a patient's health. The graphical user interface can be configured to display the information associated with the patient on one or more user interface screens.

19 Claims, 34 Drawing Sheets

(51) Int. Cl.
*G06F 3/04817* (2022.01)
*G06F 3/04847* (2022.01)

(52) U.S. Cl.
CPC .............. *A61B 5/746* (2013.01); *A61M 16/06* (2013.01); *G06F 3/04817* (2013.01); *A61M 2205/3334* (2013.01); *A61M 2205/505* (2013.01); *A61M 2205/584* (2013.01)

(58) Field of Classification Search
CPC .......... A61M 16/06; A61M 2205/3334; A61M 2205/505; A61M 2205/584
See application file for complete search history.

(56) References Cited

U.S. PATENT DOCUMENTS

| | | |
|---|---|---|
| 6,543,449 B1 | 4/2003 | Woodring et al. |
| D590,414 S | 4/2009 | Bhat et al. |
| 7,623,888 B1 | 11/2009 | Wolter |
| 7,736,132 B2 | 6/2010 | Bliss et al. |
| D630,641 S | 1/2011 | Bamford |
| 8,006,691 B2 | 8/2011 | Kenyon et al. |
| D645,469 S | 9/2011 | Gardner et al. |
| 8,020,551 B2 | 9/2011 | Virr et al. |
| 8,028,693 B2 | 10/2011 | Trevor-Wilson et al. |
| 8,042,535 B2 | 10/2011 | Kenyon et al. |
| D667,837 S | 9/2012 | Magee et al. |
| D667,838 S | 9/2012 | Magee et al. |
| 8,576,191 B2 | 11/2013 | Knott et al. |
| D701,233 S | 3/2014 | Heong et al. |
| D705,798 S | 5/2014 | Lim et al. |
| D706,286 S | 6/2014 | Pitt |
| D720,767 S | 1/2015 | Miller et al. |
| 8,944,057 B2 | 2/2015 | Hill et al. |
| 9,031,793 B2 * | 5/2015 | Lynn ..................... G16H 20/17 702/19 |
| 9,038,631 B2 | 5/2015 | Bath et al. |
| 9,038,632 B2 | 5/2015 | Crumblin et al. |
| 9,072,848 B2 | 7/2015 | Bertinetti et al. |
| 9,072,860 B2 | 7/2015 | Lithgow et al. |
| 9,089,659 B2 | 7/2015 | Wallace et al. |
| D745,023 S | 12/2015 | Kwon |
| 9,227,035 B2 | 1/2016 | Crumblin et al. |
| 9,229,630 B2 | 1/2016 | Altas et al. |
| D757,040 S | 5/2016 | Zankowski et al. |
| D760,275 S | 6/2016 | Zhang |
| 9,358,359 B2 | 6/2016 | Lithgow et al. |
| D764,506 S | 8/2016 | Rathke et al. |
| 9,539,409 B2 | 1/2017 | Crumblin et al. |
| D781,897 S | 3/2017 | Umezawa et al. |
| 9,607,495 B2 | 3/2017 | Tivig et al. |
| 9,610,420 B2 | 4/2017 | Lithgow et al. |
| D787,531 S | 5/2017 | Wada |
| D788,128 S | 5/2017 | Wada |
| D788,143 S | 5/2017 | Wada |
| 9,737,675 B2 | 8/2017 | Frame et al. |
| RE46,543 E | 9/2017 | Trevor-Wilson et al. |
| D806,735 S | 1/2018 | Olsen et al. |
| D811,425 S | 2/2018 | Olsen et al. |
| D824,410 S | 7/2018 | Grubbs et al. |
| D824,939 S | 8/2018 | Sagrillo et al. |
| D825,590 S | 8/2018 | Sagrillo et al. |
| 10,046,128 B2 | 8/2018 | Hill et al. |
| D831,048 S | 10/2018 | Sagrillo et al. |
| 10,105,506 B2 | 10/2018 | Bassin et al. |
| 10,149,952 B2 | 12/2018 | Bertinetti et al. |
| D837,230 S | 1/2019 | Johnston et al. |
| 10,201,676 B2 | 2/2019 | Lithgow et al. |
| 10,293,125 B2 | 5/2019 | Jeha et al. |
| 10,342,950 B2 | 7/2019 | Bath et al. |
| D876,451 S | 2/2020 | Rawohl et al. |
| D876,452 S | 2/2020 | Rawohl et al. |
| D876,456 S | 2/2020 | Broughton et al. |
| D885,414 S | 5/2020 | Bilancio et al. |
| D896,834 S | 9/2020 | Kawaichi et al. |
| 10,758,692 B2 | 9/2020 | Frame et al. |
| D912,078 S | 3/2021 | Pellow et al. |
| D914,039 S | 3/2021 | Zimmerman et al. |
| D930,035 S | 9/2021 | Evans et al. |
| D942,494 S | 2/2022 | Broughton et al. |
| D946,025 S | 3/2022 | Vogler-Ivashchanka et al. |
| D946,617 S | 3/2022 | Ahmed |
| D949,904 S | 4/2022 | Hsu et al. |
| D950,584 S | 5/2022 | Huang et al. |
| D954,718 S | 6/2022 | Evans et al. |
| D955,414 S | 6/2022 | Tompkins et al. |
| D955,415 S | 6/2022 | Bennett et al. |
| 11,373,000 B1 | 6/2022 | Babani et al. |
| 11,497,879 B2 | 11/2022 | Bath et al. |
| D978,157 S | 2/2023 | Han et al. |
| 2007/0265877 A1 | 11/2007 | Rice et al. |
| 2008/0099017 A1 | 5/2008 | Bordewick et al. |
| 2008/0183057 A1 | 7/2008 | Taube |
| 2008/0228464 A1 | 9/2008 | Al-Onaizan et al. |
| 2009/0055735 A1 | 2/2009 | Zaleski et al. |
| 2009/0149927 A1 | 6/2009 | Kneuer et al. |
| 2010/0030797 A1 | 2/2010 | Johnson et al. |
| 2010/0224192 A1 * | 9/2010 | Dixon ................ A61B 5/14539 128/204.23 |
| 2010/0298718 A1 | 11/2010 | Gilham et al. |
| 2011/0067697 A1 * | 3/2011 | Lellouche .............. A61M 16/10 128/204.23 |
| 2012/0030611 A1 * | 2/2012 | Skidmore ........... A61M 16/024 715/777 |
| 2013/0006129 A1 * | 1/2013 | Muir ................... A61B 5/14551 600/500 |
| 2013/0283197 A1 | 10/2013 | Skidmore |
| 2014/0190485 A1 | 7/2014 | Milne et al. |
| 2015/0094865 A1 | 4/2015 | Choi et al. |
| 2015/0097701 A1 | 4/2015 | Al-Ali et al. |
| 2015/0121315 A1 * | 4/2015 | Glenn ..................... G06F 3/0488 715/863 |
| 2016/0199612 A1 | 7/2016 | Foote et al. |
| 2016/0256642 A1 * | 9/2016 | Soysa ............... A61M 16/1075 |
| 2016/0310691 A1 | 10/2016 | Bath et al. |
| 2017/0087327 A1 | 3/2017 | Crumblin et al. |
| 2017/0136198 A1 | 5/2017 | Delangre et al. |
| 2017/0161461 A1 | 6/2017 | Delangre et al. |
| 2017/0182270 A1 | 6/2017 | Kenyon et al. |
| 2017/0182278 A1 | 6/2017 | Allen |
| 2017/0239432 A1 | 8/2017 | Delangre et al. |
| 2018/0036543 A1 * | 2/2018 | Delisle ................ A61N 1/3904 |
| 2018/0099109 A1 * | 4/2018 | Kinsky ..................... A61B 5/08 |
| 2018/0232528 A1 | 8/2018 | Williamson et al. |
| 2018/0333550 A1 | 11/2018 | Hill et al. |
| 2018/0339122 A1 * | 11/2018 | Lunz .................. A63B 21/0087 |
| 2018/0369522 A1 | 12/2018 | Bassin et al. |
| 2019/0125999 A1 * | 5/2019 | Häussermann ....... A61M 16/10 |
| 2019/0134325 A1 | 5/2019 | Bertinetti et al. |
| 2020/0054520 A1 * | 2/2020 | Johnson ................ A61B 5/091 |
| 2020/0054846 A1 * | 2/2020 | Eriksson ........... A61M 16/0051 |
| 2020/0188615 A1 * | 6/2020 | Troili ................ A61M 16/0069 |
| 2021/0077758 A1 | 3/2021 | Frame et al. |
| 2021/0181932 A1 | 6/2021 | Han et al. |
| 2023/0350557 A1 * | 11/2023 | Han .................... A61B 5/7425 |

FOREIGN PATENT DOCUMENTS

| | | |
|---|---|---|
| WO | WO 2013/189538 A1 | 12/2013 |
| WO | WO 14/205513 | 12/2014 |
| WO | WO 17/079798 | 5/2017 |
| WO | WO 2018/156804 A1 | 8/2018 |

OTHER PUBLICATIONS

Extended European Search Report for European Patent Application No. 18885477.2, dated Jul. 2, 2021, in 8 pages.
"Modes of Mechanical Ventilation" [retrieved from the internet on Apr. 12, 2019].

* cited by examiner

GRAPHICAL USER INTERFACE FOR A FLOW THERAPY APPARATUS

INCORPORATION BY REFERENCE TO ANY PRIORITY APPLICATIONS

Any and all applications for which a foreign or domestic priority claim is identified in the Application Data Sheet as filed with the present application are incorporated by reference under 37 CFR 1.57 and made a part of this specification.

FIELD OF THE DISCLOSURE

The present disclosure relates to graphical user interfaces for controlling a flow therapy apparatus.

BACKGROUND

Respiratory apparatuses are used in various environments such as hospital, medical facility, residential care, or home environments to deliver a flow of gas to users or patients. A respiratory apparatus, or a flow therapy apparatus, may include an oxygen inlet to allow delivery of supplemental oxygen with the flow of gas, and/or a humidification apparatus to deliver heated and humidified gases. A graphical user interface can be used to display the characteristics of the gases flow, including flow rate, temperature, gas concentration, such as oxygen concentration, humidity, pressure, etc.

SUMMARY

In accordance with certain features, aspects and advantages of at least one of the embodiments disclosed herein, a breathing assistance apparatus comprising: a housing; a display; one or more processors configured with computer readable instructions to: generate a graphical user interface on the display, the graphical user interface comprising: a parameter display section comprising a first plurality of parameter display elements, each parameter display element configured to display a parameter value associated with a parameter of the breathing assistance apparatus, wherein the first plurality of parameter display elements are positioned in a first configuration to substantially fill the parameter display section; receive an input to include an additional parameter display element within the parameter display section, wherein the additional parameter display element is associated with an additional parameter; modify the parameter display section to include the additional parameter display element associated with the additional parameter, wherein modifying the parameter display section includes, generating the additional parameter display element within the parameter display section; modifying a shape of one or more of the first plurality of parameter display elements; and positioning the first plurality of parameter display elements and the additional parameter display element within the parameter display section forming a second plurality of parameter display elements, wherein the second plurality of parameter display elements are positioned in a second configuration within the parameter display section.

In some configurations, wherein the input is an indication that a peripheral device has been added to the breathing assistance apparatus.

In some configurations, the indication is automatically generated after the peripheral device is detected by the breathing assistance apparatus.

In some configurations, the peripheral device is at least one of a pulse oximeter, a CO2 sensor, or a pressure sensor.

In some configurations, the peripheral device is a pulse oximeter.

In some configurations, the additional parameter is at least one of blood oxygen saturation of the patient, pulse rate, respiration rate, perfusion index, CO2 concentration, or pressure.

In some configurations, the second plurality of parameter display elements substantially fill the parameter display section.

In some configurations, the computer readable instructions further configure the processor to arrange parameter display elements based on a priority value associated with each parameter.

In some configurations, the computer readable instructions further configure the processor to display a visual indication of a confidence value associated with a parameter of a parameter display element of the second plurality of parameter display elements.

In some configurations, the visual indication changes the color of a displayed parameter value of the parameter display element.

In some configurations, when the confidence value drops below a threshold, the parameter value is no longer displayed.

In some configurations, the computer readable instructions further configure the processor to transition from a first operational mode to a second operational mode when a parameter value exceeds or drops below a threshold associated with a parameter associated with one of the parameter display elements of the second plurality of parameter display elements, and display a visual indication of the transition from the first operational mode to the second operational mode.

In some configurations, the computer readable instructions further configure the processor to display a graphical user interface comprising input controls configured to receive input from a user to change operational values of a parameter.

In some configurations, after operational parameter values of a parameter are modified, the parameter display element of the parameter provides a graphical indication indicating the breathing assistance apparatus is adjusting the parameter until the parameter has moved to the modified value.

In some configurations, each parameter display element is associated with a different color.

In some configurations, each parameter display element displays the units for the parameter associated with the parameter display element.

In some configurations, the displayed value of the parameter is larger than the display of the units.

In some configurations, the apparatus comprises an ambient light sensor configured to detect ambient light, wherein the computer readable instructions further configure the processor to automatically adjust the brightness of the display based on the output of the ambient light sensor.

In some configurations, the input is user input, wherein the graphical user interface is configured to receive a selection from a user of a parameter for adding to the parameter display section.

In some configurations, for a first parameter display element of the first plurality of parameter display elements, the parameter value is a first parameter value and the parameter is a first parameter of the breathing assistance apparatus, wherein the first parameter display element is configured to display a second parameter value associated with a second parameter of the breathing assistance apparatus in conjunction with the first parameter value of the first parameter.

In some configurations, the display of the first parameter value is larger than the display of the second parameter value.

In some configurations, the first parameter is a primary parameter and the second parameter is a secondary parameter, wherein the secondary parameter is related to the primary parameter.

In some configurations, the primary parameter and the secondary parameter are both determined based on data received from a first patient sensor.

In accordance with certain features, aspects and advantages of at least one of the embodiments disclosed herein, a method comprising: generating a graphical user interface on a display of a breathing assistance apparatus, the graphical user interface comprising a parameter display section comprising a first plurality of parameter display elements, each parameter display element configured to display a parameter value associated with a parameter of the breathing assistance apparatus, wherein the first plurality of parameter display elements are positioned in a first configuration to substantially fill the parameter display section; receiving an input to include an additional parameter display element within the parameter display section, wherein the additional parameter display element is associated with an additional parameter; generating the additional parameter display element within the parameter display section; modifying a shape of one or more of the first plurality of parameter display elements; and positioning the first plurality of elements and the additional parameter display element within the parameter display section forming a second plurality of parameter display elements, wherein the second plurality of parameter display elements are positioned in a second configuration within the parameter display section.

In some configurations, the input is an indication that a peripheral device has been added to the breathing assistance apparatus, In some configurations, the indication is automatically generated after the peripheral device is detected by the breathing assistance apparatus.

In some configurations, the additional parameter is a patient parameter measured by the peripheral device.

In some configurations, the peripheral device is at least one of a pulse oximeter, a CO2 sensor, or a pressure sensor.

In some configurations, the additional parameter at least one of blood oxygen saturation of the patient, pulse rate, respiration rate, perfusion index, CO2 concentration, or pressure.

In some configurations, the second plurality of elements substantially fill the parameter display section in the second configuration.

In some configurations, the method comprises arranging parameter display elements based on a priority value associated with each parameter.

In some configurations, the method comprises displaying a visual indication of a confidence value associated with a parameter of a parameter display element of the second plurality of parameter display elements.

In some configurations, the visual indication changes the color of the parameter value.

In some configurations, the method comprises no longer displaying a parameter value when a confidence value for the parameter drops below a threshold.

In some configurations, the method comprises transitioning from an automatic operational mode to a manual operational mode when a parameter value exceeds or drops below a threshold associated with a parameter associated with one of the parameter display elements of the second plurality of parameter display elements, and displaying a visual indication of the transition from the automatic operational mode to the manual operational mode.

In some configurations, the method comprises displaying a graphical user interface comprising input controls configured to receive input from a user to change operational values of a parameter.

In some configurations, after operational parameter values of a parameter are modified based on input received from the user, the parameter display element of the parameter provides a graphical indication indicating the breathing assistance apparatus is adjusting the parameter until the parameter has moved to the modified value.

In some configurations, each parameter display element is associated with a different color.

In some configurations, each parameter display element displays the units for the parameter associated with the parameter display element.

In some configurations, the displayed value of the parameter is larger than the display of the units.

In some configurations, the method comprises an ambient light sensor configured to detect ambient light, wherein the computer readable instructions further configure the processor to automatically adjust the brightness of the display based on the output of the ambient light sensor.

In some configurations, receiving input comprises receiving a selection from a user of a parameter for adding to the parameter display section.

In some configurations, for a first parameter display element of the first plurality of parameter display elements, the parameter value is a first parameter value and the parameter is a first parameter of the breathing assistance apparatus, wherein the method further comprises displaying, by the first parameter display element, a second parameter value associated with a second parameter of the breathing assistance apparatus in conjunction with the first parameter value of the first parameter.

In some configurations, the display of the first parameter value is larger than the display of the second parameter value.

In some configurations, the first parameter is a primary parameter and the second parameter is a secondary parameter, wherein the secondary parameter is related to the primary parameter.

In some configurations, the primary parameter and the secondary parameter are both determined based on data received from a first patient sensor.

In accordance with certain features, aspects and advantages of at least one of the embodiments disclosed herein, a breathing assistance apparatus comprising: a housing; a display; one or more processors configured with computer readable instructions to: generate a graphical user interface on the display, the graphical user interface comprising: a parameter display section comprising a first plurality of parameter display elements, each parameter display element associated with a parameter of the breathing assistance apparatus, wherein the first plurality of parameter display elements are positioned in a first configuration during a first mode of operation; receive an indication that the breathing assistance apparatus has entered a second mode of operation; and provide a linking indicator visually linking two or more parameter display elements forming linked parameter display elements during the second mode of operation.

In some configurations, the computer readable instructions further configure the processor to display operational limits for each of linked parameter display elements associated with the second mode of operation.

In some configurations, the computer readable instructions further configure the processor to display a visual indicator providing an indication of the current value of the parameter relative to the operational limits.

In some configurations, visually linking the two or more parameter display elements includes changing the shape of at least one of the linked parameter display elements.

In some configurations, visually linking the two or more parameter display elements includes removal of a gap between the two or more parameter display elements.

In some configurations, the linking indicator is a border encapsulating the linked parameter display elements.

In some configurations, the operational limits are displayed for least one of the parameters associated with the linked parameter display elements during the second mode of operation.

In some configurations, the apparatus comprises an ambient light sensor configured to detect ambient light, wherein the computer readable instructions further configure the processor to automatically adjust the brightness of the display based on the output of the ambient light sensor.

In some configurations, for a first parameter display element of the first plurality of parameter display elements, the parameter value is a first parameter value and the parameter is a first parameter of the breathing assistance apparatus, wherein the first parameter display element is configured to display a second parameter value associated with a second parameter of the breathing assistance apparatus in conjunction with the first parameter value of the first parameter.

In some configurations, the display of the first parameter value is larger than the display of the second parameter value.

In some configurations, the first parameter and the second parameter are both determined based on data received from a first patient sensor.

In some configurations, a first parameter display element of the linked parameter display elements is blood oxygen saturation and a second parameter display element of the linked parameter display elements is oxygen concentration.

In accordance with certain features, aspects and advantages of at least one of the embodiments disclosed herein, a method comprising: generating a graphical user interface on the display of a breathing assistance apparatus, the graphical user interface comprising a parameter display section comprising a first plurality of parameter display elements, each parameter display element associated with a parameter of the breathing assistance apparatus, wherein the first plurality of parameter display elements are positioned in a first configuration during a first mode of operation; receiving an indication that the breathing assistance apparatus has entered a second mode of operation; and providing a linking indicator visually linking two or more parameter display elements forming linked parameter display elements during the second mode of operation.

In some configurations, a first parameter display element of the linked parameter display elements is blood oxygen saturation and a second parameter display element of the linked parameter display elements is oxygen concentration.

In some configurations, the method comprises displaying operational limits for each of linked parameter display elements associated with the second mode of operation.

In some configurations, the method comprises further comprising displaying a visual indicator providing an indication of the current value of the parameter relative to the operational limits.

In some configurations, the method comprises changing the shape of at least one of the linked parameter display elements when providing the linking indicator.

In some configurations, the linking indicator is a border encapsulating the linked parameter display elements.

In some configurations, the method comprises displaying operational limits associated with at least one of the linked parameter display elements during the second mode of operation.

In some configurations, visually linking the two or more parameter display elements includes removal of a gap between the two or more parameter display elements.

In some configurations, the method comprises detecting ambient light with an ambient light sensor and automatically adjusting the brightness of the display based on the output of the ambient light sensor.

In some configurations, for a first parameter display element of the first plurality of parameter display elements, the parameter value is a first parameter value and the parameter is a first parameter of the breathing assistance apparatus, wherein the method further comprises displaying, by the first parameter display element, a second parameter value associated with a second parameter of the breathing assistance apparatus in conjunction with the first parameter value of the first parameter.

In some configurations, the display of the first parameter value is larger than the display of the second parameter value.

In some configurations, the first parameter and the second parameter are both determined based on data received from a first patient sensor.

Features from one or more embodiments or configurations may be combined with features of one or more other embodiments or configurations. Additionally, more than one embodiment may be used together during a process of respiratory support of a patient.

The term 'comprising' as used in this specification means 'consisting at least in part of'. When interpreting each statement in this specification that includes the term 'comprising', features other than that or those prefaced by the term may also be present. Related terms such as 'comprise' and 'comprises' are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

It should be understood that alternative embodiments or configurations may comprise any or all combinations of two or more of the parts, elements or features illustrated, described or referred to in this specification.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

DETAILED DESCRIPTION

Flow Therapy Apparatus

Figure 1:
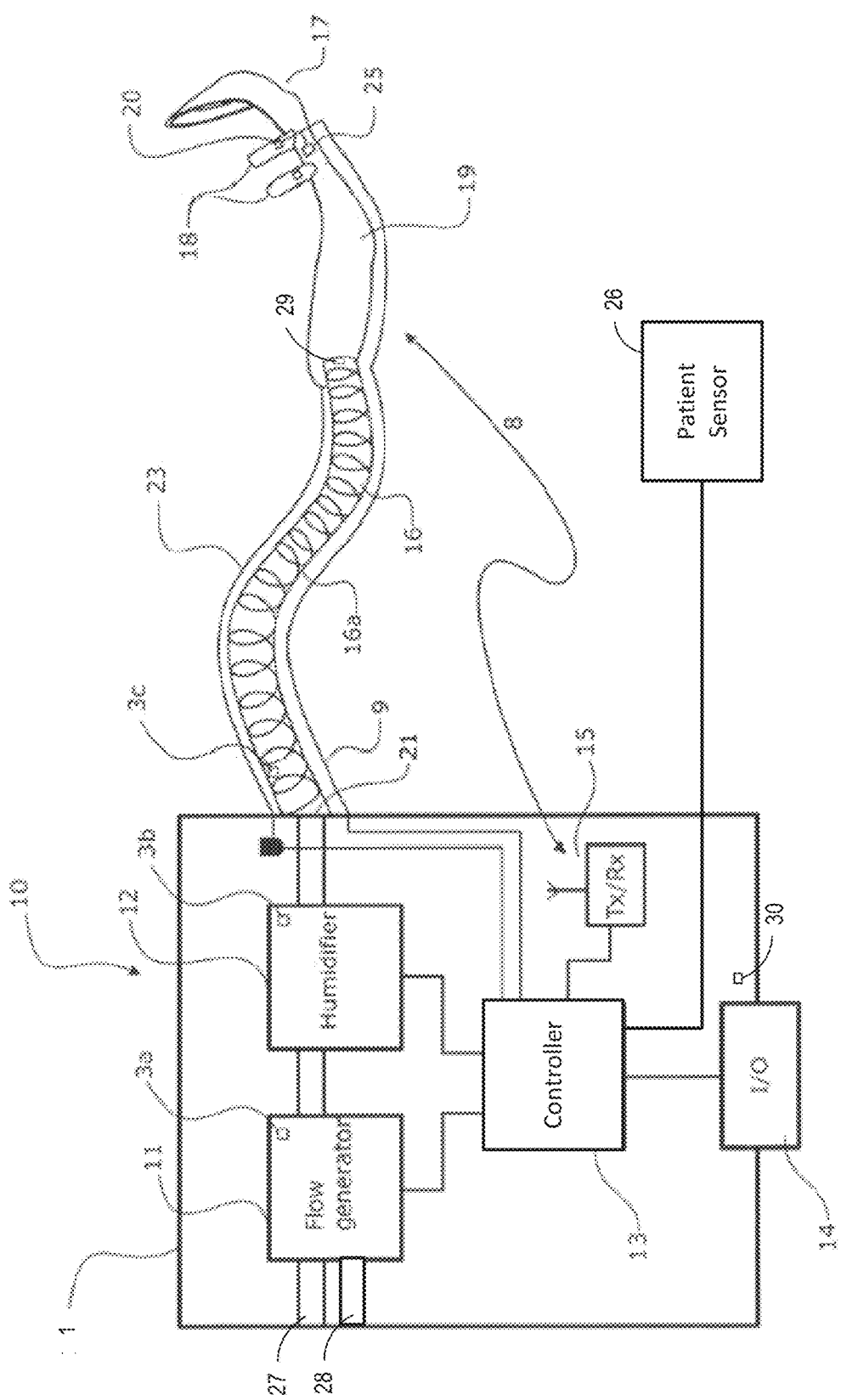
FIG. 1 shows in diagrammatic form a flow therapy apparatus.

A flow therapy apparatus 10 is shown in FIG. 1. The flow therapy apparatus can refer to any type of breathing assistance or respiratory apparatus that can be used to deliver a flow of gases to users or patients. For example, the flow therapy apparatus can include, without limitation, apparatuses that are configured to provide high flow therapy, non-invasive ventilation (NIV), continuous positive airway pressure (CPAP), bilevel positive airway pressure, minimally invasive ventilation (MIV), and/or other types of breathing assistance therapies. The apparatus 10 can comprise a main housing 1 that contains a flow generator 11 in the form of a motor/impeller arrangement (for example, a blower), an optional humidifier 12, a controller 13, and a user interface 14 (comprising, for example, a display and input device(s) such as button(s), a touch screen, or the like). The controller 13 can be configured or programmed to control the operation of the apparatus. For example, the controller can control components of the apparatus, including but not limited to: operating the flow generator 11 to create a flow of gas (gases flow) for delivery to a patient, operating the humidifier 12 (if present) to humidify and/or heat the generated gases flow, control a flow of oxygen into the flow generator blower, receiving user input from the user interface 14 for reconfiguration and/or user-defined operation of the apparatus 10, and outputting information (for example on the display) to the user. In some configurations, the flow of oxygen can be entrained into the flow therapy apparatus downstream of the blower. The user can be a patient, healthcare professional, or anyone else interested in using the apparatus. As used herein, a "gases flow" can refer to any flow of gases that may be used in the breathing assistance or respiratory device, such as a flow of ambient air, a flow comprising substantially 100% oxygen, a flow comprising some combination of ambient air and oxygen, and/or the like.

A patient breathing conduit 16 is coupled at one end to a gases flow outlet 21 in the housing 1 of the flow therapy apparatus 10. The patient breathing conduit 16 is coupled at another end to a patient interface 17 such as a non-sealed nasal cannula with a manifold 19 and nasal prongs 18. Additionally, or alternatively, the patient breathing conduit 16 can be coupled to a face mask, a nasal mask, a nasal pillows mask, an endotracheal tube, a tracheostomy interface, and/or the like. The gases flow that is generated by the flow therapy apparatus 10 may be humidified, and delivered to the patient via the patient conduit 16 through the cannula 17. The patient conduit 16 can have a heater wire 16a to heat gases flow passing through to the patient. The heater wire 16a can be under the control of the controller 13. The patient conduit 16 and/or patient interface 17 can be considered part of the flow therapy apparatus 10, or alternatively peripheral to it. The flow therapy apparatus 10, breathing conduit 16, and patient interface 17 together can form a flow therapy system.

The controller 13 can control the flow generator 11 to generate a gases flow of the desired flow rate. The controller 13 can also control a supplemental oxygen inlet valve to allow for delivery of supplemental oxygen, the humidifier 12 (if present) can humidify the gases flow and/or heat the gases flow to an appropriate level, and/or the like. The gases flow is directed out through the patient conduit 16 and cannula 17 to the patient. The controller 13 can also control a heating element in the humidifier 12 and/or the heating element 16a in the patient conduit 16 to heat the gas to a desired temperature for a desired level of therapy and/or level of comfort for the patient. The controller 13 can be programmed with or can determine a suitable target temperature of the gases flow.

The oxygen inlet port 28 can include a valve through which a pressurized gas may enter the flow generator or blower. The valve can control a flow of oxygen into the flow generator blower. The valve can be any type of valve, including a proportional valve or a binary valve. The source of oxygen can be an oxygen tank or a hospital oxygen supply. Medical grade oxygen is typically between 95% and 100% purity. Oxygen sources of lower purity can also be used. Examples of valve modules and filters are disclosed in U.S. Provisional Application No. 62/409,543, titled "Valve Modules and Filter", filed on Oct. 18, 2016, and U.S. Provisional Application No. 62/488,841, titled "Valve Modules and Filter", filed on Apr. 23, 2017, which are hereby incorporated by reference in their entireties.

The flow therapy apparatus 10 can measure and control the oxygen content of the gas being delivered to the patient, and therefore the oxygen content of the gas inspired by the patient. In configurations where high flow therapy is used, the high flow rate of gas delivered meets or exceeds the peak inspiratory demand of the patient. This means that the volume of gas delivered by the device to the patient during inspiration meets, or is in excess of, the volume of gas inspired by the patient during inspiration. High flow therapy therefore helps to prevent entrainment of ambient air when the patient breathes in, as well as flushing the patient's airways of expired gas. So long as the flow rate of delivered gas meets or exceeds peak inspiratory demand of the patient, entrainment of ambient air is prevented, and the gas delivered by the device is substantially the same as the gas the patient breathes in. As such, the oxygen concentration measured in the device, fraction of delivered oxygen (FdO2), would be substantially the same as the oxygen concentration the user is breathing, fraction of inspired oxygen (FiO2), and as such the terms may can be seen as equivalent.

Operation sensors 3a, 3b, 3c, such as flow, temperature, humidity, and/or pressure sensors can be placed in various locations in the flow therapy apparatus 10. Additional sensors (for example, sensors 20, 25) may be placed in various locations on the patient conduit 16 and/or cannula 17 (for example, there may be a temperature sensor 29 at or near the end of the inspiratory tube). Output from the sensors can be received by the controller 13, to assist the controller in operating the flow therapy apparatus 10 in a manner that provides suitable therapy. In some configurations where high flow therapy is used, providing suitable therapy includes meeting a patient's peak inspiratory demand. The apparatus 10 may have a transmitter and/or receiver 15 to enable the controller 13 to receive signals 8 from the sensors and/or to control the various components of the flow therapy apparatus 10, including but not limited to the flow generator 11, humidifier 12, and heater wire 16a, or accessories or peripherals associated with the flow therapy apparatus 10. Additionally, or alternatively, the transmitter and/or receiver 15 may deliver data to a remote server or enable remote control of the apparatus 10.

Oxygen may be measured by placing one or more gas composition sensors (such as an ultrasound transducer system) after the oxygen and ambient air have finished mixing. The measurement can be taken within the device, the delivery conduit, the patient interface, or at any other suitable location.

Oxygen concentration may also be measured by using flow rate sensors on at least two of the ambient air inlet conduit, the oxygen inlet conduit, and the final delivery conduit to determine the flow rate of at least two gases. By determining the flow rate of both inlet gases or one inlet gas and one total flow rate, along with the assumed or measured oxygen concentrations of the inlet gases (about 20.9% for ambient air, about 100% for oxygen), the oxygen concentration of the final gas composition can be calculated. Alternatively, flow rate sensors can be placed at all three of the ambient air inlet conduit, the oxygen inlet conduit, and the final delivery conduit to allow for redundancy and testing that each sensor is working correctly by checking for consistency of readings. Other methods of measuring the oxygen concentration delivered by the flow therapy apparatus 10 can also be used.

The flow therapy apparatus 10 can include an ambient light sensor 30. The ambient light sensor 30 can be located close to the user interface 14. The ambient light sensor 30 can allow the flow therapy apparatus 10 to automatically alter the brightness of the screen based on the level of ambient light. This can be particularly beneficial as the device may be used at home or in a hospital ward where people are sleeping.

The flow therapy apparatus 10 can include a patient sensor 26, such as a pulse oximeter, to measure one or more physiological parameters of the patient, such as a patient's blood oxygen saturation (SpO2), heart rate, respiratory rate, perfusion index, and provide a measure of signal quality. The patient sensor 26 may be referred to as a peripheral device. The sensor 26 can communicate with the controller 13 through a wired connection or by communication through a wireless transmitter on the sensor 26. The sensor 26 may be a disposable adhesive sensor designed to be connected to a patient's finger. The sensor 26 may be a non-disposable sensor. Sensors are available that are designed for different age groups and to be connected to different locations on the patient, which can be used with the flow therapy apparatus. The pulse oximeter would be attached to the user, typically at their finger, although other places such as an earlobe are also an option. The pulse oximeter would be connected to a processor in the device and would constantly provide signals indicative of the patient's blood oxygen saturation. In some configurations, the patient sensor 26 can be a carbon dioxide (CO2) sensor or a pressure sensor. The CO2 sensor can measure the concentration of exhaled CO2. The pressure sensor can measure ambient pressure, pressure at the patient interface or pressure in the flow path.

Some types of flow therapy apparatuses can provide high flow therapy, which may be administered to the nares of a user and/or orally, or via a tracheostomy interface. High flow therapy may deliver gases to a user at a flow rate at or exceeding the intended user's peak inspiratory flow requirements. The high flow therapy may generate a flushing effect in the nasopharynx such that the anatomical dead space of the upper airways is flushed by the high incoming gases flow. This can create a reservoir of fresh gas available for each and every breath, while minimizing re-breathing of nitrogen and carbon dioxide. Meeting inspiratory demand and flushing the airways is additionally important when trying to control the patient's FdO2. High flow therapy can be delivered with a non-sealing patient interface such as, for example, a nasal cannula. The nasal cannula may be configured to deliver breathing gases to the nares of a user at a flow rate exceeding the intended user's peak inspiratory flow requirements.

The flow generator or blower 11 can include an ambient air inlet port 27 to entrain ambient room air into the blower through. The flow therapy apparatus 10 may also include an oxygen inlet port 28 leading to a valve through which a pressurized gas may enter the flow generator or blower 11. The valve can control a flow of oxygen into the flow generator blower 11. The valve can be any type of valve, including a proportional valve or a binary valve.

The blower can operate at a motor speed of greater than about 1,000 RPM and less than about 30,000 RPM, greater than about 2,000 RPM and less than about 21,000 RPM, or between any of the foregoing values. Operation of the blower can mix the gases entering the blower through the inlet ports. Using the blower as the mixer can decrease the pressure drop that would otherwise occur in a system with a separate mixer, such as a static mixer comprising baffles, because mixing requires energy. In some configurations, the oxygen may be entrained into the flow therapy apparatus downstream of the blower.

The flow therapy apparatus can use closed loop control, which allows a patient or clinician to set a target SpO2 instead of a target FdO2. The flow therapy apparatus can automatically alter the FdO2 of the flow therapy apparatus to achieve the targeted SpO2 based on values of target SpO2, current SpO2, and current FdO2. Automatically controlling the FdO2 can help to quickly and accurately adjust the FdO2 until a target SpO2 is achieved. The system can generate a patient specific model for each patient at the initiation of a therapy session. In some configurations, the system may continuously update the patient model throughout the therapy session. The flow therapy apparatus can have greater precision in achieving the targeted SpO2 by adjusting the FdO2, as needed, to stay within the targeted SpO2 range, without being constantly monitored by a clinician. The target values can also be referred to as operational values.

The present disclosure provides for a flow therapy apparatus that can implement a closed loop oxygen control system. Features of the closed loop oxygen control system may be combined with features of one or more configurations disclosed herein.

The flow therapy apparatus may operate in automatic mode or manual mode. In automatic mode, the controller can automatically control the FdO2 based on a target FdO2 determined based on the target SpO2, and in manual mode, the controller can receive a target FdO2 from a clinician or patient, such as via a user interface. In automatic mode or manual mode, a valve at the oxygen inlet may be connected to the controller that can control the oxygen concentration in gases flow based on a target FdO2. The controller can execute a control algorithm that can continually measure FdO2 output by the flow therapy apparatus. The controller can continue to adjust the valve at the oxygen inlet until the measured FdO2 arrives at the target FdO2. The measured FdO2 may be determined by a gases composition sensor.

The flow therapy apparatus may be configured to change from automatic mode to manual mode when the SpO2 of the patient is not within an acceptable patient range. In some instances, the flow therapy apparatus automatically reverts to manual mode when the SpO2 of the patient is outside of the patient limits (above or below) or if the patient's SpO2 did not move within the limits within a defined period of time after the start of the therapy session. The flow therapy apparatus may revert to manual mode when the signal quality of the patient sensor is below a threshold level for a defined period of time. In some configurations, the flow therapy apparatus may trigger an alarm when it switches from automatic mode to manual mode. In some configurations, the flow therapy apparatus may trigger an alarm, but the flow therapy apparatus does not automatically switch from automatic mode to manual mode. The triggered alarm may generate an option, which the user may select, in order to disable automatic mode and revert to manual mode. In such a configuration, the alarm may be minimized and the flow therapy apparatus may continue to operate in automatic mode until the user manually switches the flow therapy apparatus from automatic mode to manual mode. The alarm mode interface is further discussed herein with respect to, at least, FIGS. 7A-7C.

The closed loop oxygen control system may utilize two control loops. The first control loop may be implemented by an SpO2 controller. The SpO2 controller can determine a target FdO2 based in part on the target SpO2. As discussed above, the target SpO2 value can be a single value or a range of acceptable values. The value(s) could be pre-set, chosen by a clinician, or determined automatically based on patient characteristics. Generally, target SpO2 values are received or determined before or at the beginning of a therapy session, though target SpO2 values may be received at any time during the therapy session. During a therapy session, the SpO2 controller can also receive as inputs: measured FdO2 reading(s) from a gases composition sensor, and measured SpO2 reading(s) and a signal quality reading(s) from the patient sensor. Based at least in part on the inputs, the SpO2 controller can output a target FdO2 to the second control loop.

The second control loop may be implemented by the FdO2 controller. The FdO2 controller can receive inputs of measured FdO2 and target FdO2. The FdO2 controller can then output an oxygen inlet valve control signal to control the operation of the oxygen valve based on a difference between these measured FdO2 and target FdO2 values. The FdO2 controller may receive the target FdO2 value that is output from the first control loop when the flow therapy apparatus is operating in automatic mode. The FdO2 controller may also receive additional parameters such as flow rate values, gas properties, and/or measured FdO2. From at least some of the inputs, the FdO2 controller can determine an oxygen flow rate that would be required to achieve the target FdO2. The FdO2 controller can use the flow rate input in order to alter the valve control signal. If the flow rate changes, the FdO2 controller can automatically calculate a new required oxygen flow rate required to maintain the target FdO2 at the new flow rate without having to wait for feedback from the gas concentration sensor, such as the measured FdO2 value. The FdO2 controller can then output the altered valve control signal to control the valve based on the new flow rate. In some configurations, the control signal of the FdO2 controller may set the current of the oxygen valve in order to control operation of the oxygen valve. Additionally, or alternatively, the FdO2 controller could detect changes to the measured FdO2 and alter the position of the valve accordingly. During manual mode, the second control loop can operate independently without receiving the target FdO2 from the first control loop. Rather, the target FdO2 can be received from user input or a default value.

During the automatic mode, the flow therapy apparatus can enter a learning phase where the controller generates a patient specific model. After the learning phase, the flow therapy apparatus operates in the control phase using the patient specific model until the end of the therapy session or until the flow therapy apparatus enters manual mode. The flow therapy apparatus may update the patient specific model continuously throughout the therapy session. In such a configuration, the flow therapy apparatus may forego the learning phase entirely. Further examples of a closed loop control system are disclosed in International Application No. PCT/NZ2018/050137, titled "Closed Loop Oxygen Control", filed on Oct. 4, 2018, which is hereby incorporated by reference in its entirety.

User Interface

FIGS. 2A-8F illustrate examples of graphical user interfaces 100 for the user interface 14 of the flow therapy apparatus 10. The graphical user interface 100 can provide a display of flow therapy treatment information and indicators of a patient's health. The flow therapy apparatus 10 can be configured to display the information associated with the patient on one or more user interface screens. Each screen of the user interface 100 can be configured to display one or more indicators associated with the flow therapy session and the patient.

The graphical user interface 100 allows the operator to control operation of the flow therapy apparatus 100. The graphical user interface 100 may include a touch screen. A touch screen allows for a user to directly interact with elements of the graphical user interface 100. The graphical user interface 100 may include a plurality of buttons for interacting with flow therapy apparatus. Other types of user input devices, such as a mouse, keyboard, stylus, and/or other devices may be used to interact with the user interface screen.

Figure 2A:
FIG. 2A-B illustrates a graphical user interface of a flow therapy apparatus.
Figure 2B:
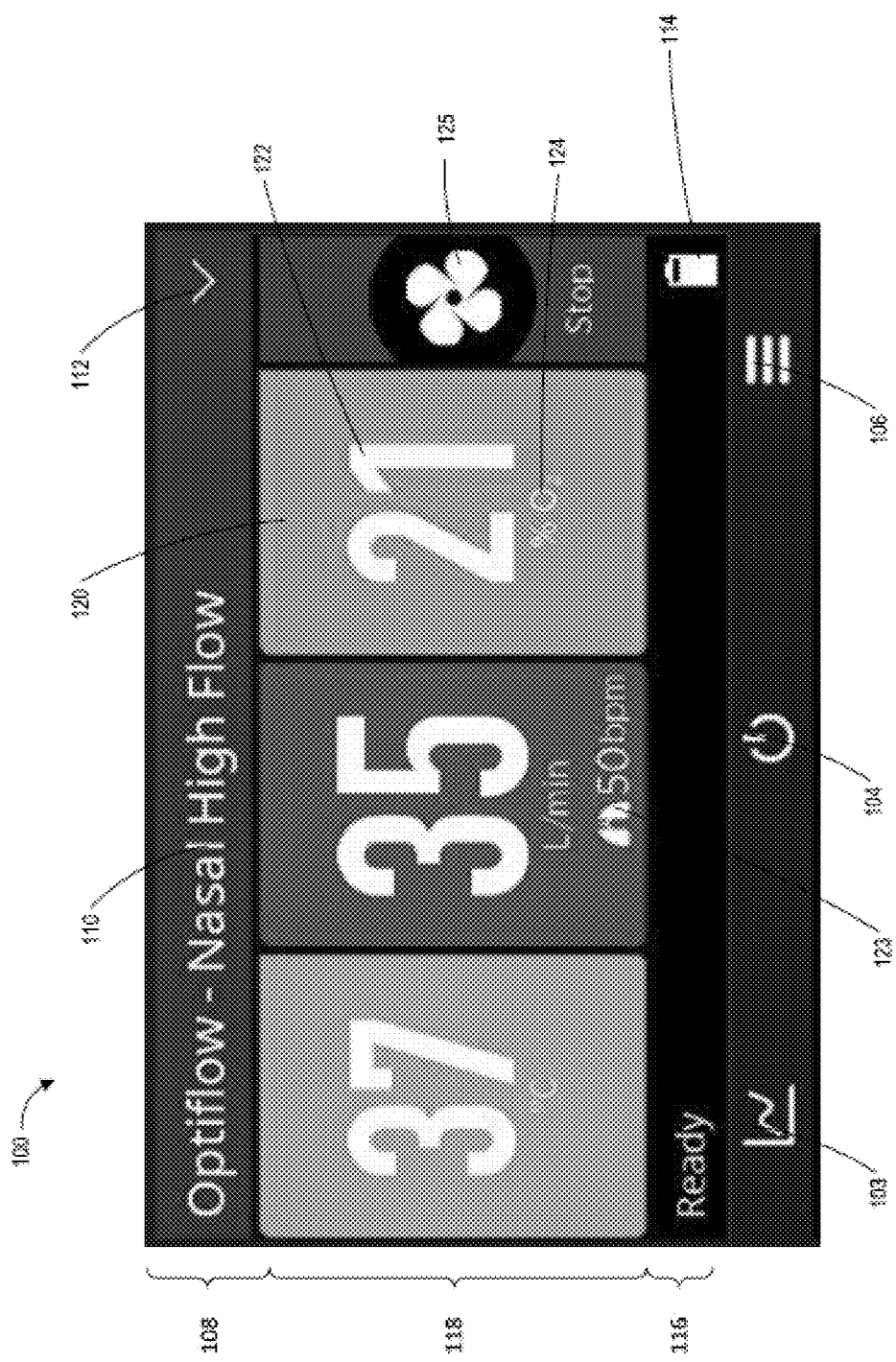

With reference to FIGS. 2A and 2B, the graphical user interface 100 may include one or more buttons along the bottom of the display, which could include a back button 102, a trend button 103, a power button 104, and/or a menu button 106. In the configuration illustrated in FIG. 2B, the back button 102 is replaced by a trend button 103. In such a configuration, when appropriate, the back button 102 may be provided at a different location within the graphical user interface 100. One or more of the buttons 102, 103, 104, 106 may be graphical elements within the graphical user interface 100. One or more of the buttons 102, 103, 104, 106 may be separated from the screen and the graphical user interface 100. The buttons may be capacitive. The buttons 102, 103, 104, 106 can be sealed so that they do not have any gaps or cracks, thereby preventing ingress of water and other particles.

One or more of the buttons at the bottom of the display 102, 103, 104, 106 can be configured to include physical identification features such that a user can identify and/or distinguish the buttons by touch. The buttons may be indented, protruded, and/or have a different texture on the surface. This would allow a user to identify and/or distinguish the buttons when the visual identification features of the buttons are not visible, such as when the device is being used in the dark. In some configurations, only a subset of the buttons includes physical identification features. For example, the power button may be the only button to include physical identification features. This could allow the user to easily locate the power button in the dark to wake up the device and turn on the screen. In some configurations, one or more buttons could be backlit and/or could glow in the dark.

The physical identification features can be used to identify the location of the buttons. Additionally, the physical identification features can be different for each button, such that a user can use the physical identification features to distinguish between the buttons. The physical identification features may be shaped such that they are similar to the visual symbols of each button.

The physical identification features can be located on the button itself, which would allow the physical identification feature to indicate the exact location of the button. Alternatively, the physical identification features may be located adjacent to the button (such as, above or below, or on the housing). This would allow a user to identify and/or distinguish the button without inadvertently pressing it, particularly if the button was capacitive.

The graphical user interface 100 may include an upper display portion 108, such as a bar. The upper display portion 108 may be divided into one or more subsections. The upper display portion 108 may display an operational mode element 110 that displays the current mode of operation. A mode selection element 112 can be configured to display available modes of operation and allow a user to switch between the available modes. The upper display portion 108 may include an indication of the battery level 114, such as illustrated in FIG. 2A. The top bar portion 108 may also include additional elements, such as a device settings element. The device settings may be accessible through a menu button. The device settings may be configured to be generally inaccessible to a user as they may be used for configuration of the device and are not meant to be changed later. For example, the device settings may be password protected.

Figure 7A:
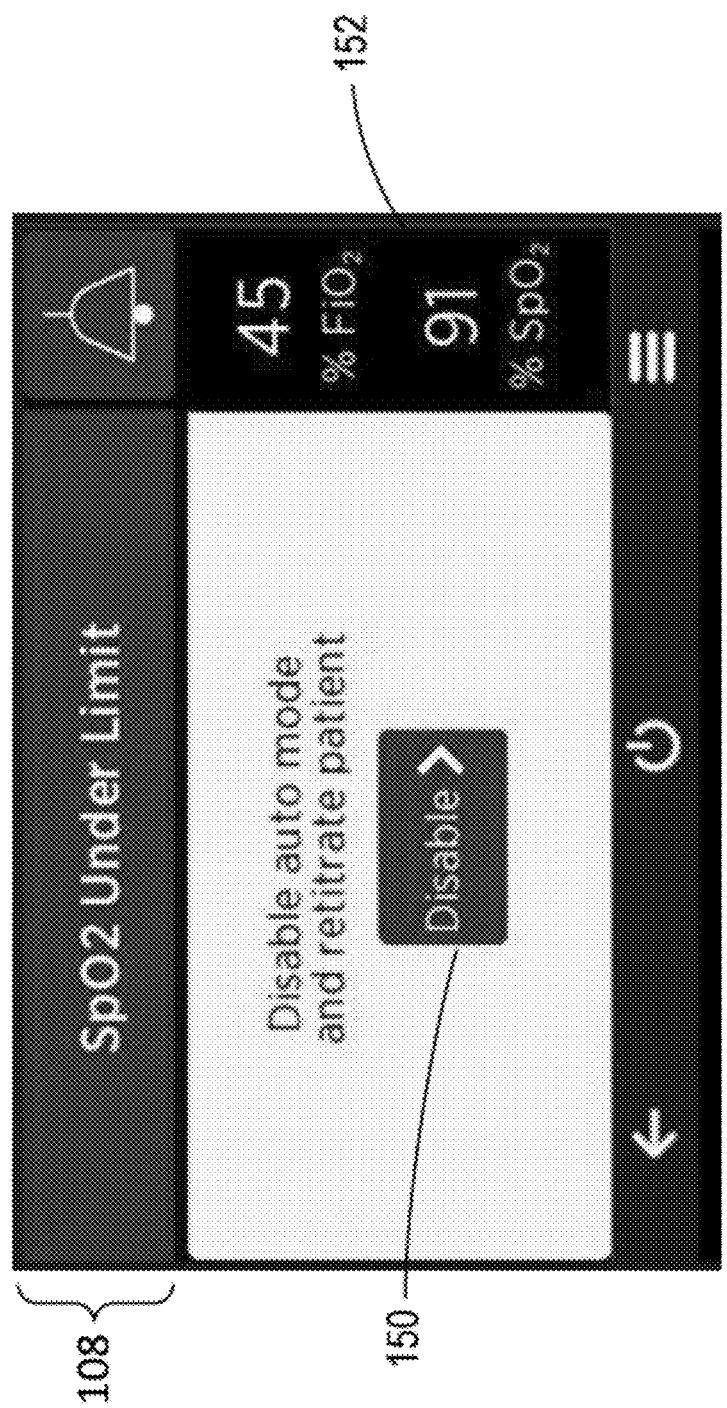
FIG. 7A-7C illustrates a graphical user interface of a flow therapy apparatus for an alarm condition.
Figure 7B:
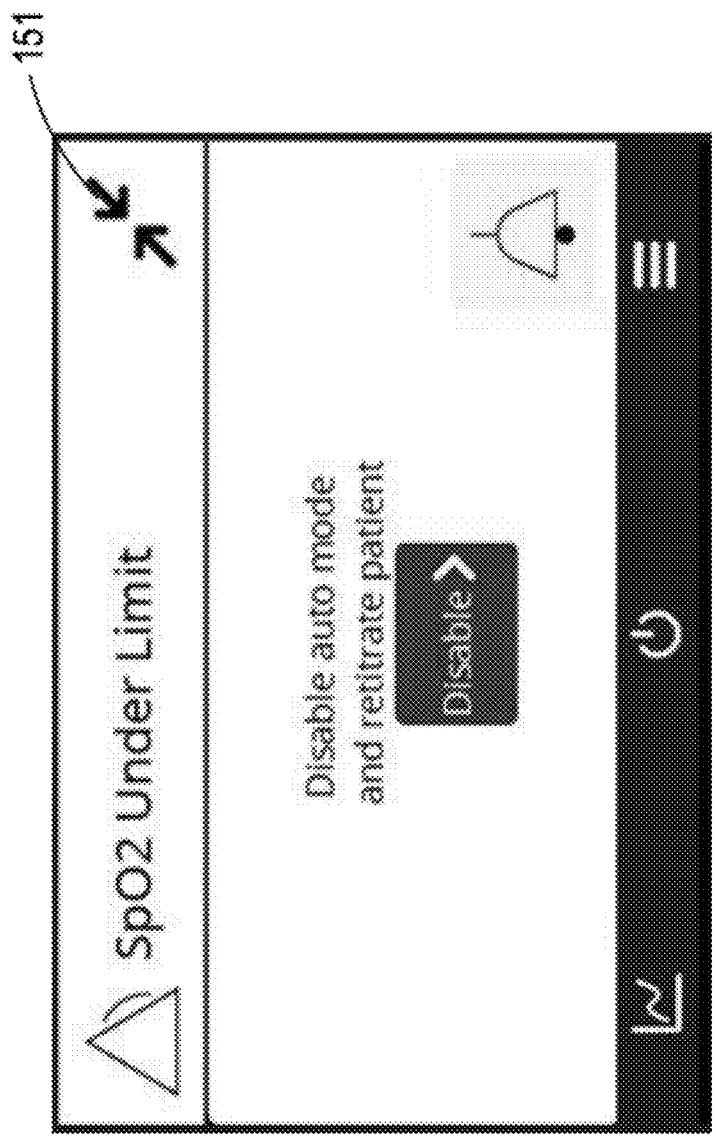
Figure 7C:
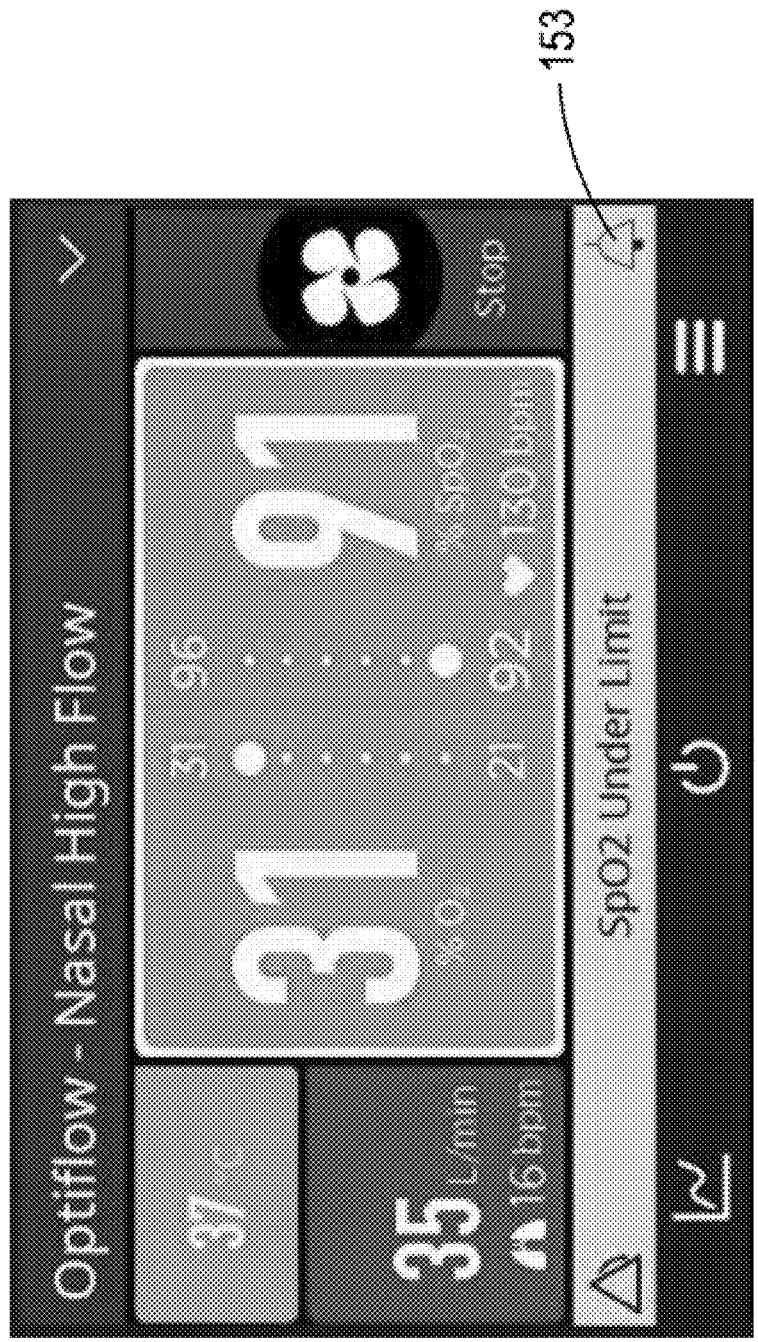

The graphical user interface 100 may include a lower display portion 116 along the bottom of the screen. The lower display portion 116 can display notifications to the user. The notifications can be related to the current status of the device, such as confirming that a command is being carried out. The lower display portion 116 may display warnings to the user. These warnings may initially be full screen warnings that can then be minimised to the lower display portion 116 (such as illustrated in FIGS. 7A-7C). The lower display portion 116 may then have a further indicator that the warning is still present. In one configuration, the lower display portion 116 can flash yellow until the warning has been resolved. In some configurations, the alarm screen may automatically maximize after a set amount of time after the alarm screen was minimized or after the user last interacted with the flow therapy apparatus. The lower display portion 116 may have an indication of whether the flow therapy apparatus is in standby mode or operating mode. For example, the lower display portion 116 can be yellow when the device is in standby, with an accompanying statement or indicator. The lower display portion 116 may include an indication of the battery level 114, such as illustrated in FIG. 2B. In some configurations, the lower display portion may include an indication that the flow therapy apparatus is communicatively coupled to another device, such as through USB, WiFi, GSM, Bluetooth, and/or other wired or wireless communication interfaces.

The graphical user interface 100 can include a central or main display portion 118 positioned between the upper display portion 108 and lower display portion 116. The main display portion 118 can include a plurality of parameter display elements 120. The parameter display elements 120 can also be referred to as parameter elements or parameter tiles. Each parameter display element 120 can correspond to a device or patient parameter. Each type of patient or device parameter can be associated with a specific colour (e.g., flow rate can be blue and FiO2 can be green, etc.). By associating specific colours with each parameter, users can quickly recognize the types of parameters being displayed by the graphical user interface 100. The graphical user interface 100 can have a start/stop tile 125 (such as illustrated in FIG. 2B). The start/stop tile 125 can be used to toggle between therapy mode and standby mode. The start/stop tile 125 can additionally have a graphical indication of whether the device is in therapy mode or standby mode. In the configuration in FIG. 2B, the tile 125 has a fan icon. In standby mode, the fan icon can be grey and stationary. In therapy mode, the fan icon can be white and rotates. The start/stop tile 125 may include text to indicate whether the device is in therapy or standby mode.

A parameter display element 120 can include a parameter value 122 and a parameter label 124. The parameter value 122 can be a number representing the value of the parameter, and a parameter label 124 can display the units for a parameter. The units of the parameter are constant. The units can provide an indication of what the parameter display element represents. For example, L/Min would indicate that the parameter is flowrate. The label can be configured to display a name or nickname associated with the parameter in addition to or in lieu of the units for the parameter. For example, the parameter label 124 may alternate between the units and the nickname. The label 124 may be smaller than the parameter value 122. In some configurations, a parameter display element may include a second device or patient parameter 123. The second parameter 123 can include a corresponding parameter value and label (which may include a unit and/or icon for the parameter). In the configuration illustrated in FIG. 2B, the second parameter 123 is respiratory rate and it is incorporated in the flow rate tile. In the illustrated configuration, the respiratory rate is accompanied by an icon (such as a pair of lungs) to indicate what this number represents. When a second parameter cannot be measured, this section of the parameter display element can remain blank. For example, no second parameter value or label may be displayed, such as illustrated in FIG. 2A. When the second parameter can be measured, it can be automatically displayed in the parameter display element without modifying the configuration of parameter display elements on the main display portion 118. This can be advantageous, as the alternative would be to have a parameter display element that is occasionally blank, or to have the layout of the parameter display elements constantly changing based on whether or not a second parameter (such as, respiratory rate or another parameter) can be measured.

The larger parameter within the parameter display element 120 can be referred to as the primary parameter. The primary parameter of a parameter display element may always be displayed, sometimes even if there is not a current parameter value to display (such as, the parameter display element in FIG. 4A). The second parameter may be referred to as a secondary parameter when the second parameter is related to or dependent upon a primary parameter. The primary and secondary parameters may be grouped, coupled, or otherwise related based on relationships between the parameters and/or sensors used for measuring the parameters. For example, SpO2 and pulse rate may be grouped together because both parameters could be measured using the same patient sensor, such as a pulse oximeter.

The parameter display elements can have different units of measurement associated with each parameter. For example, some non-limiting examples of units for various parameters are as follows:
Oxygen Concentration:
FiO2, FdO2, O2 (also including a % sign, a decimal value, or using partial pressure of oxygen)
Oxygen Saturation:
SpO2, SaO2
Flow Rate:
L/min, LPM, L·min−1, liters per minute.
Respiratory Rate:
RR, BPM, Breaths/minute
Temperature:
° C., ° F.
Pressure:
$cmH_2O$, mmHg, Pa, psi
CO2 Concentration:
CO2 (% of CO2 or partial pressure of CO2)

The parameter value 122 may be significantly larger than the parameter label 124, as illustrated in FIG. 2A. The parameter value 122 can update at a defined rate based on the parameter. For example, the flow rate may be updated periodically (e.g., every second, ever 2 seconds, etc.), aperiodically, event-based updates (e.g., when the value changes) or updated based other configuration settings. In FIG. 2A, the three parameter display elements 120 are the same size and shape. The parameter display elements 120 may have differing sizes and shapes.

The graphical user interface 100 may include a default set of parameter display elements 120 that are displayed when the flow therapy apparatus powers on. The default parameter display elements 120 may be the parameter display elements 120 displayed in FIG. 2A. The flow therapy apparatus may be configured to allow the user to determine the default parameter display elements 120 that are displayed by the graphical user interface 100. The flow therapy apparatus may allow for the user to change the positioning or order of the parameter display elements 120 within the graphical user interface 100. Each of the displayed parameter display elements may be selectable by the user. The parameter display elements 120 may have a defined number of settings that can be modified by the user. For example, the user may be able to set the operational value for the parameter or modify various display characteristics, such as, the colour, nickname, or other display characteristic associated with the parameter. The user may be able to select two or more parameters that can be displayed on a single parameter display element. In some configurations, the user may select a primary parameter for display and a secondary parameter for display. In such a configuration, the secondary parameters available for display may be limited to parameters that are related to the primary parameter (for example, parameters that are measured using the same patient sensor).

In FIG. 2A the graphical user interface 100 is in a landscape or horizontal orientation, however, the same design characteristics may be applied to a portrait or vertical orientation of the graphical user interface 100. For example, the illustrated layout could be rotated by 90°, in which case, the upper and lower portions could be positioned the top and bottom of the screen or alternatively the upper and lower portions could run down the sides. In a vertical orientation, the parameter display elements 120 may be stacked vertically. Each parameter display elements 120 can have the same width and height.

Figure 3A:
FIGS. 3A-3C illustrate graphical user interfaces of a flow therapy apparatus including a plurality of parameter display elements.
Figure 3B:
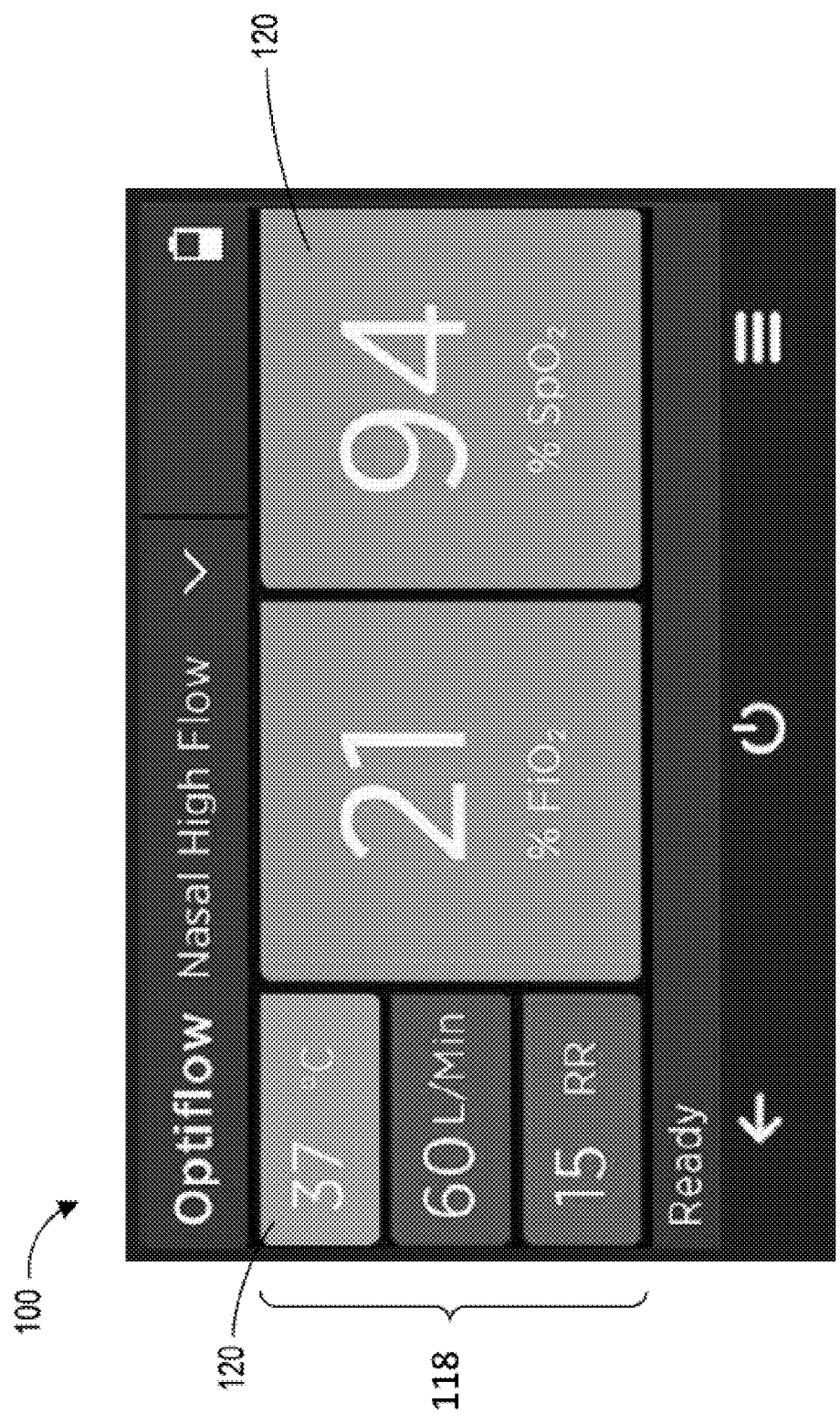

With reference to FIGS. 3A and 3B, the graphical user interface 100 can be configured to add additional parameter display elements 120 to the main display portion 118. The shape of the existing parameter display elements 120 can be automatically adjusted to accommodate the additional parameter display elements 120 within the main display portion 118. The shape of each the parameter display elements 120 can be configured to use substantially all of the available space within the main display portion 118.

Generally, a modification to the shape of a parameter display element includes modifications to shape characteristics of the parameter display element. Some examples of shape characteristics that can be modified may include: a type of shape for example, a rectangle, circle, octagon, rhomboid, custom designed shapes, or any other type of shape), dimensions of the shape (for example, height and width of a rectangle), aspect ratio, and/or other characteristics that affect the shape of the parameter display element. Other visual characteristics of the parameter display element may be modified based on a change in shape of parameter display element. For example, the formatting of icons, and/or text within the parameter display element may be dependent upon the shape of the parameter display element and can be automatically modified to accommodate the change in shape (for example, the font size will be decreased when the shape is smaller). A change in shape may refer to a change in the size and/or aspect ratio, while maintaining the same general shape of the parameter display element. In the configuration shown in FIG. 3A, the respiration rate parameter "RR" was added to the main display portion 118.

Advantages of the automatic adjustment of shape to fill the entire area can include, the display of larger parameter display elements that are easier to read, particularly when viewed from a distance. When fewer parameter display elements are present, it is preferable to utilize all the available space by changing the shape of the icons. When additional parameter display elements are added, it is then preferable change the shape of the parameter display elements such that all the parameter display elements fit on the screen. The alternative would be that not all of the display elements are visible at any one time, and the user would then need to interact with the screen in order to view them. This would result in the user not being able to view the parameters from a distance if the corresponding display elements were not already displayed on the screen. Additionally, relative sizing of the parameter display elements on the display can help to indicate the importance of the parameter. More important parameters can have a larger size relative to other parameters, which can help users to focus on the more important parameters and push the less important parameters into the background.

Additional parameter display elements 120 can be optionally displayed, such as parameter display elements 120 relating to different patient parameters. These parameter display elements 120 may be added through the settings by selecting extra parameters that the user wishes to have displayed. Additionally, or alternatively, different versions of the flow therapy apparatus may be configured to display certain parameters in accordance with specifications of the flow therapy apparatus or specific user requirements. Additionally, or alternatively, certain parameters may be displayed only when appropriate hardware is connected (for example, SpO2 may only be displayed when a pulse oximeter is connected). Additional parameters may include respiratory rate, oxygen saturation, pulse rate, CO2 concentration, pressure, and/or other parameters. In some configurations, the flow therapy apparatus may automatically add a parameter associated with a peripheral device when it is plugged into the flow therapy apparatus. For example, the flow therapy apparatus can automatically generate an indication after detecting that the peripheral device has been plugged in, and then add a parameter measured by the peripheral device to a parameter display section.

When an additional parameter is added, the parameter display elements 120 can adjust to fit with additional parameter display elements 120. The system can generate the additional parameter display element within the parameter display section. The shape of the existing parameter display elements can be modified in order to accommodate the additional parameter display element. One or more of the existing parameter display elements can be repositioned to accommodate the additional parameter display element. The new configuration of the parameter display elements can cover substantially all of main display portion 118. The layout could be similar to what is described earlier, with the parameter display elements 120 arranged side by side. Alternatively, in order to maintain desirable aspect ratios of the parameter display elements 120, the parameter display elements 120 may be arranged with some parameter display elements 120 stacked on top of each other, with the remaining parameter display elements 120 arranged side by side. Example layouts are displayed in FIGS. 3a and 3b.

FIG. 3A illustrates a sample layout for four parameter display elements 120, larger parameter display elements 120 take up a large portion and are displayed side by side, while the remaining smaller parameter display elements 120 are smaller and stacked on top of each other. Alternatively, the smaller parameter display elements 120 could be on the right side or in the middle between the larger parameter display elements 120. The larger parameter display elements 120 may be wider than the smaller parameter display elements 120, with the larger parameter display elements 120 in FIGS. 3A and 3B being shown as about twice the width of the smaller parameter display elements 120. When in the four tile arrangement (FIG. 3A), each of the larger and smaller parameter display elements 120 have roughly the same aspect ratio. When in the five tile arrangement (FIG. 3B), the smaller parameter display elements 120 have an altered aspect ratio and the units for each of the smaller parameter display elements 120 may be arranged next to the parameter value instead of below. The larger parameter display elements 120 may be determined automatically based on priority values associated with each parameter, user configuration settings, and/or system configuration settings. Each parameter can have a defined priority value. The priority value can be used to determine the position of the parameter within the display. For example, higher priority parameters can be larger blocks, whereas lower priority parameters can be smaller blocks. In FIG. 3A FiO2 and flowrate are displayed as larger parameter display elements 120.

In FIG. 3B, an additional parameter display element 120, SpO2, has been added to the main display portion 118. The layout with five parameter display elements 120 would be similar to the configuration in FIG. 3A, with two parameter display elements 120 taking up a larger amount of space, and the three remaining parameter display elements 120 stacked on top of each other on the side.

Figure 3C:

FIG. 3C illustrates a four parameter display element 120 with a start/stop tile. The SpO2 parameter display element 120 has pulse rate as a secondary parameter 123. The flow rate parameter display element 120 has respiratory rate as a secondary parameter 123. Accordingly, this layout accommodates the display of six parameters, two, of which, are secondary parameters.

FIGS. 4A-4D provide an example of the graphical user interface 100 after a patient sensor, such as a pulse oximeter measuring SpO2, has been connected to the flow therapy apparatus. The flow therapy apparatus can receive an indication that the sensor has been connected and automatically detect the type of patient sensor. The patient sensor may provide a plurality of patient parameters to the flow therapy apparatus. The layout of the graphical user interface 100 can be altered to accommodate one or more parameter display elements associated with the patient sensor. For example, a pulse oximeter may provide SpO2 data and pulse rate data, among other patient parameters. The flow therapy apparatus may automatically add the one or more parameter display elements associated with the patient sensor to the graphical user interface or the user may add the parameter(s) manually to the graphical user interface.

When a parameter of the patient sensor is unavailable (e.g., connected to the flow therapy apparatus but not connected to the patient), the flow therapy apparatus can provide an indication that the parameter value is not available to display. For example, as displayed in FIG. 4A, the value could be shown by two dashed lines instead of a parameter value. Once the patient sensor provides the parameter value, it can be displayed on the graphical user interface 100.

After a patient parameter signal is received by the patient sensor, the display of the parameter value may be delayed until a confidence value (e.g., a signal quality value) associated with the parameter satisfies a threshold. The graphical user interface 100 may be configured to provide an indication that patient parameter data is being received but is not yet ready to display. The indication may include changing the colour of the parameter value (e.g., greying out the parameter value), providing a supplemental indicator 129 (e.g., a spinning disc icon), and/or providing another indication on the graphical user interface 100. If a confidence value (e.g., signal quality) of the patient monitor drops below a defined threshold, the display of the parameter value may altered (e.g., replacing the parameter value with dashed lines or changing the colour of the parameter value).

Figure 4A:
FIGS. 4A-4D illustrate graphical user interfaces of a flow therapy apparatus that include a parameter display element associated with a patient sensor.
Figure 4B:
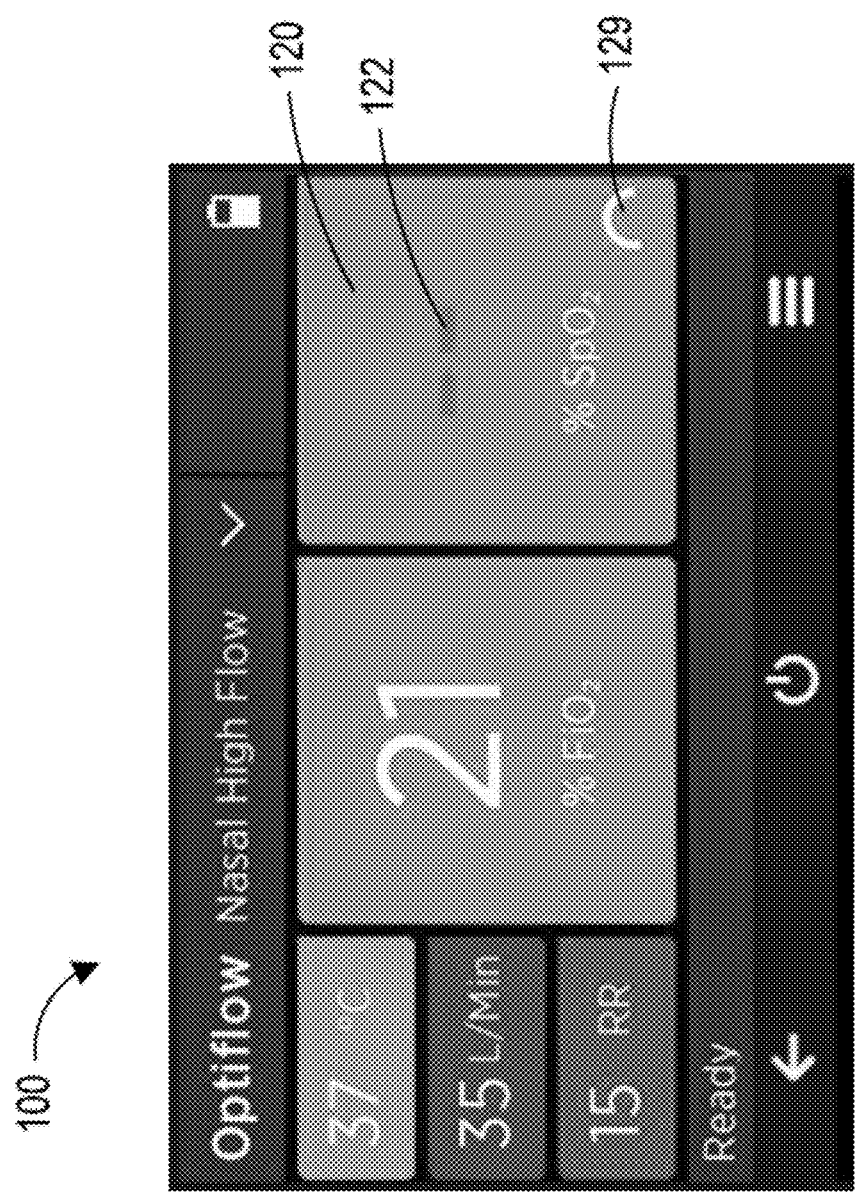
Figure 4C:
Figure 4D:
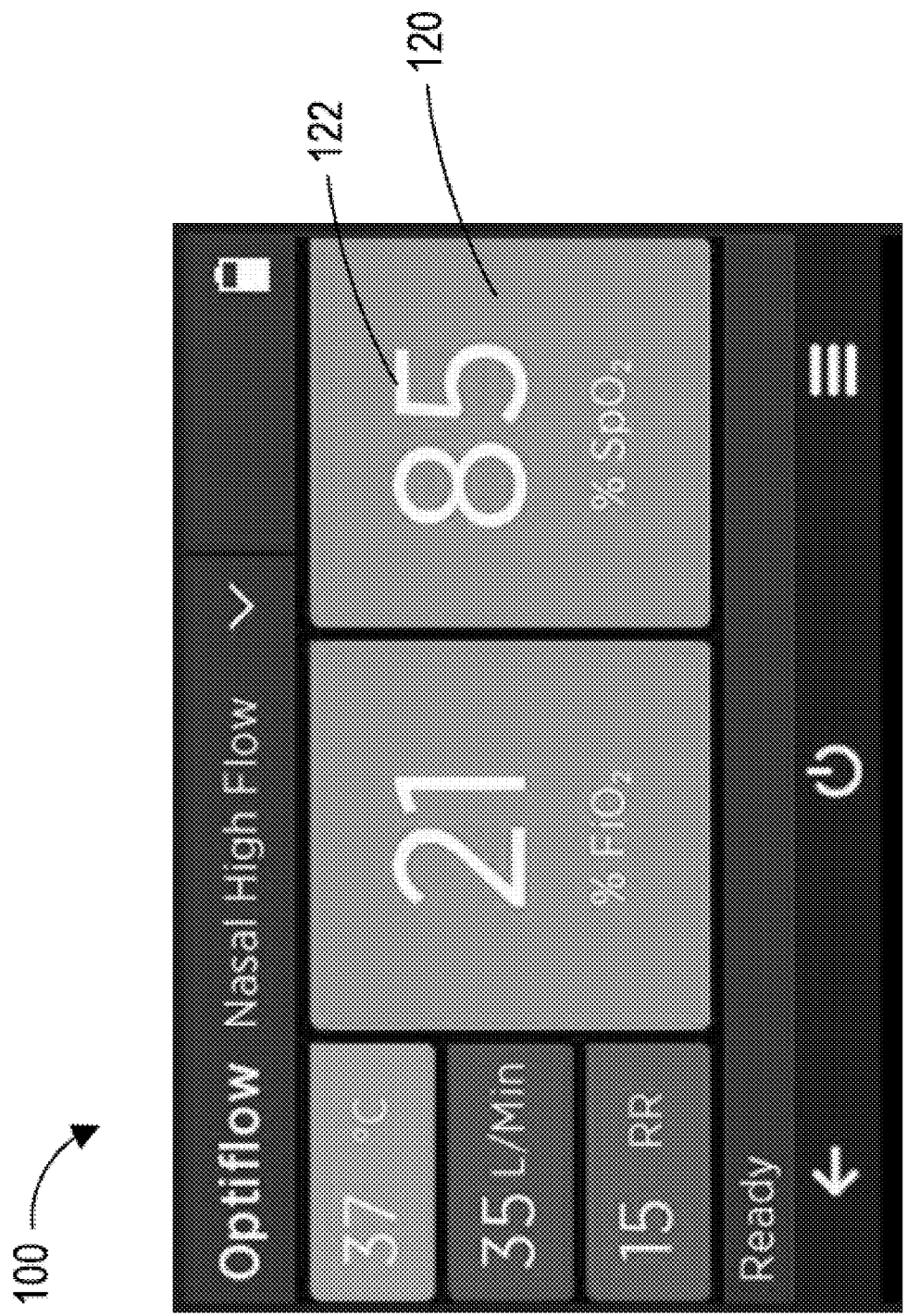

The screens depicted in FIGS. 4A-4C provide example displays illustrating various steps associated with using a patient sensor with the flow therapy apparatus. The screen depicted in FIG. 4A could be displayed when the patient sensor is connected to the flow therapy apparatus, but the patient is not wearing the patient sensor (or the patient is wearing the patient sensor but the patient cannot be detected).

The screen depicted in FIG. 4B could be displayed when the patient sensor is connected to the device and the patient is wearing the patient sensor, however the patient parameter (such as, SpO2) cannot be measured or has not yet been measured. This may be because the patient has only just recently put the patient sensor on.

The screen depicted in FIG. 4C could be displayed when the patient sensor is connected to the device, the patient is wearing the patient sensor, the patient parameter (such as, SpO2) can be measured, but the signal quality is below a threshold. The screen depicted in FIG. 4D could be displayed when the patient sensor is connected to the device, the patient is wearing the patient sensor, the patient parameter (such as, SpO2) can be measured, and the signal quality is above a threshold.

Figure 5A:
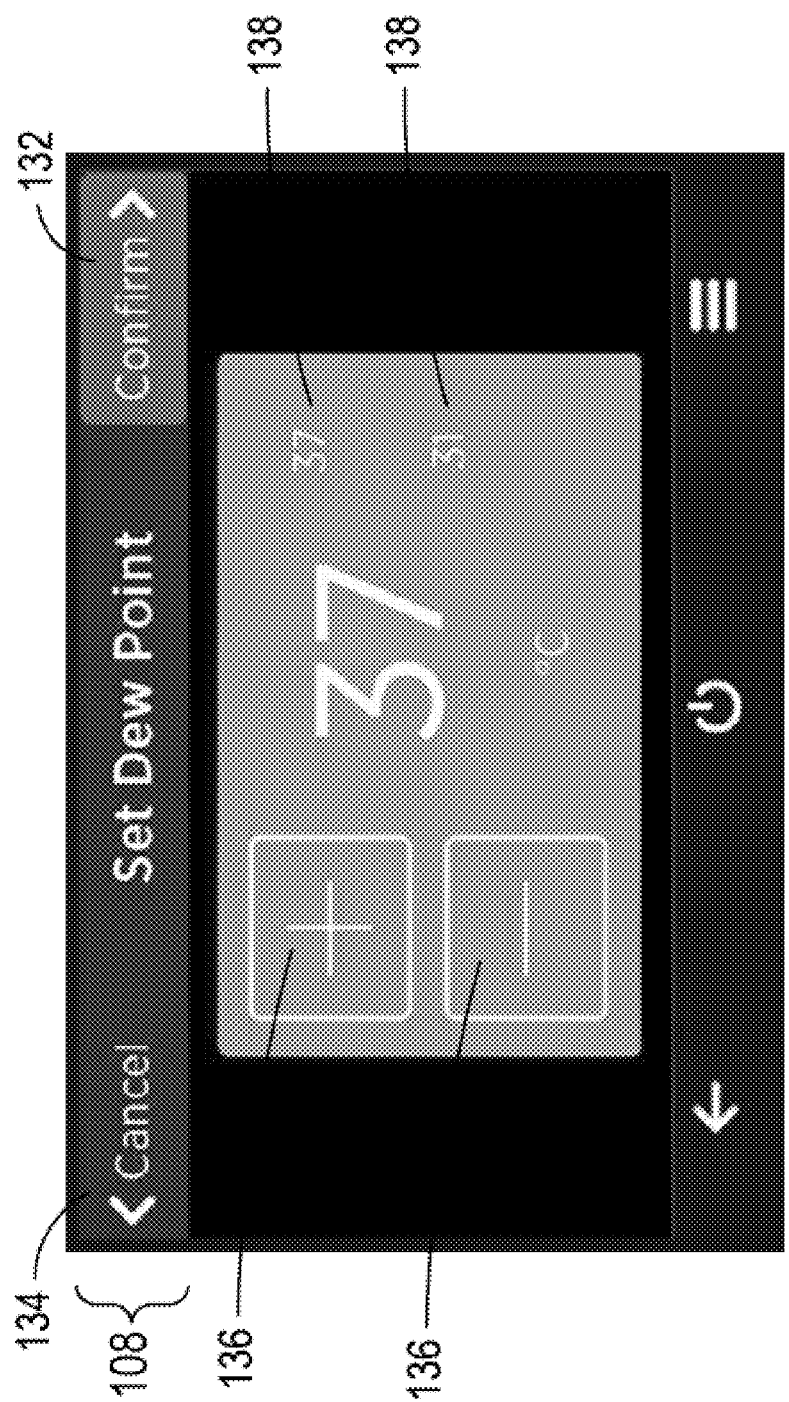
FIGS. 5A-5H illustrate graphical user interfaces of a flow therapy apparatus associated with configuration of flow parameters of the flow therapy apparatus.
Figure 5B:
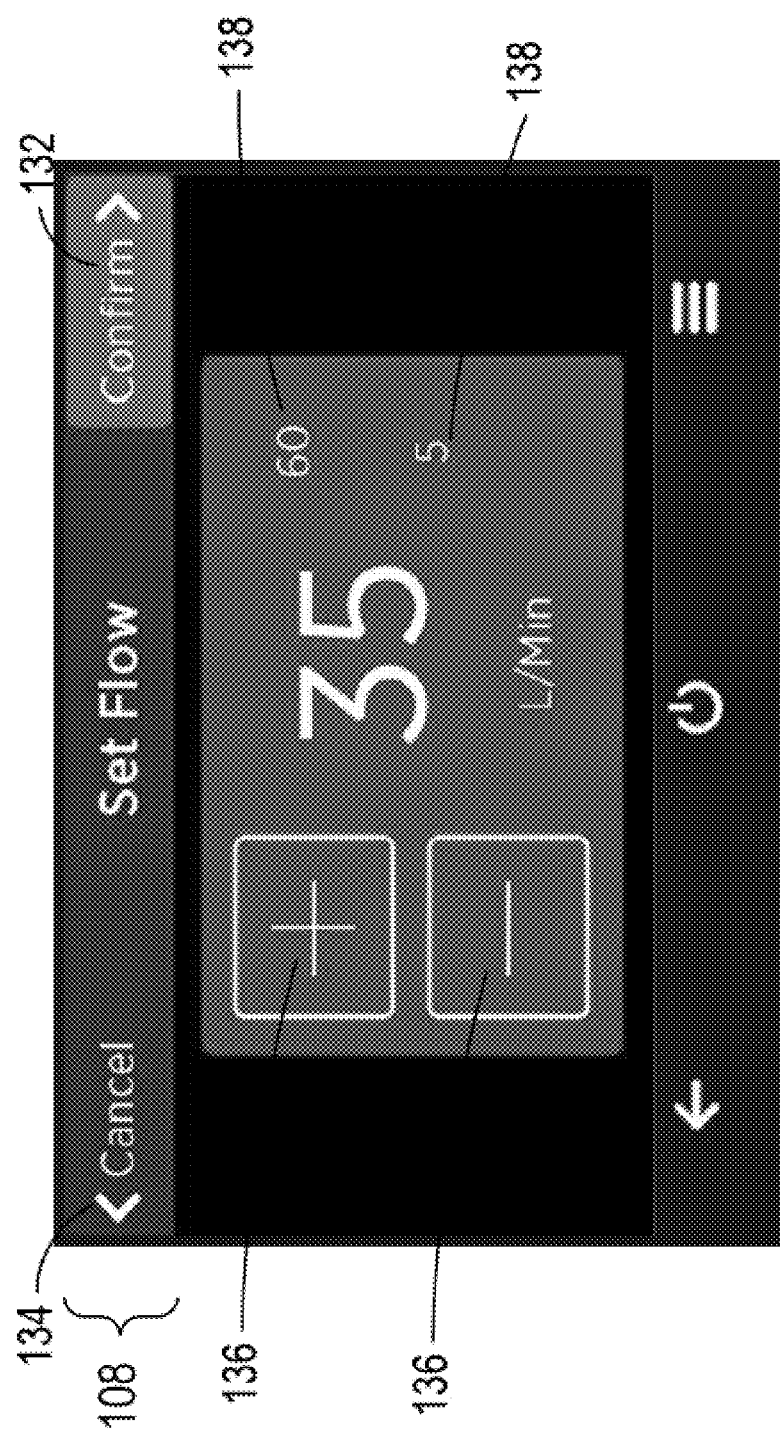
Figure 5C:
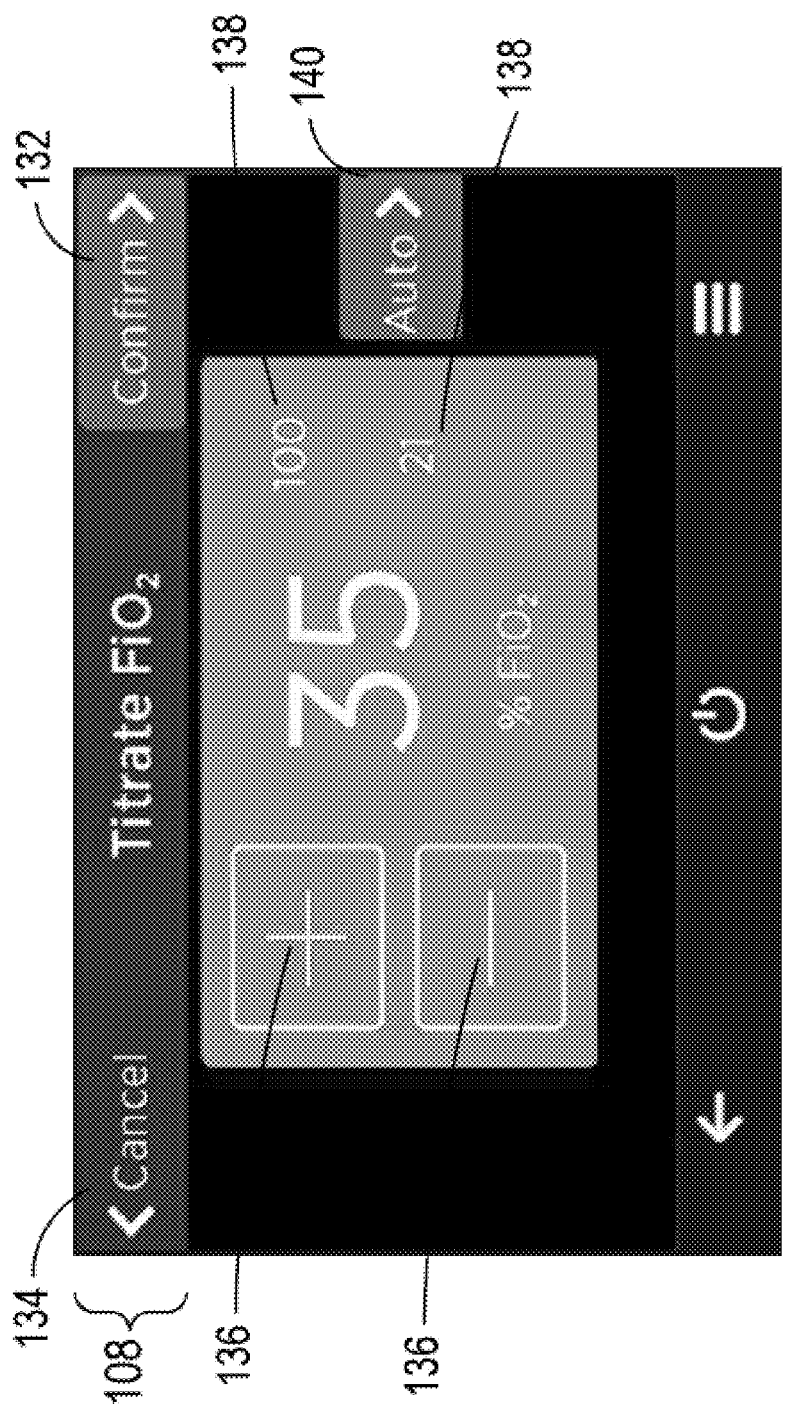
Figure 5D:
Figure 5E:
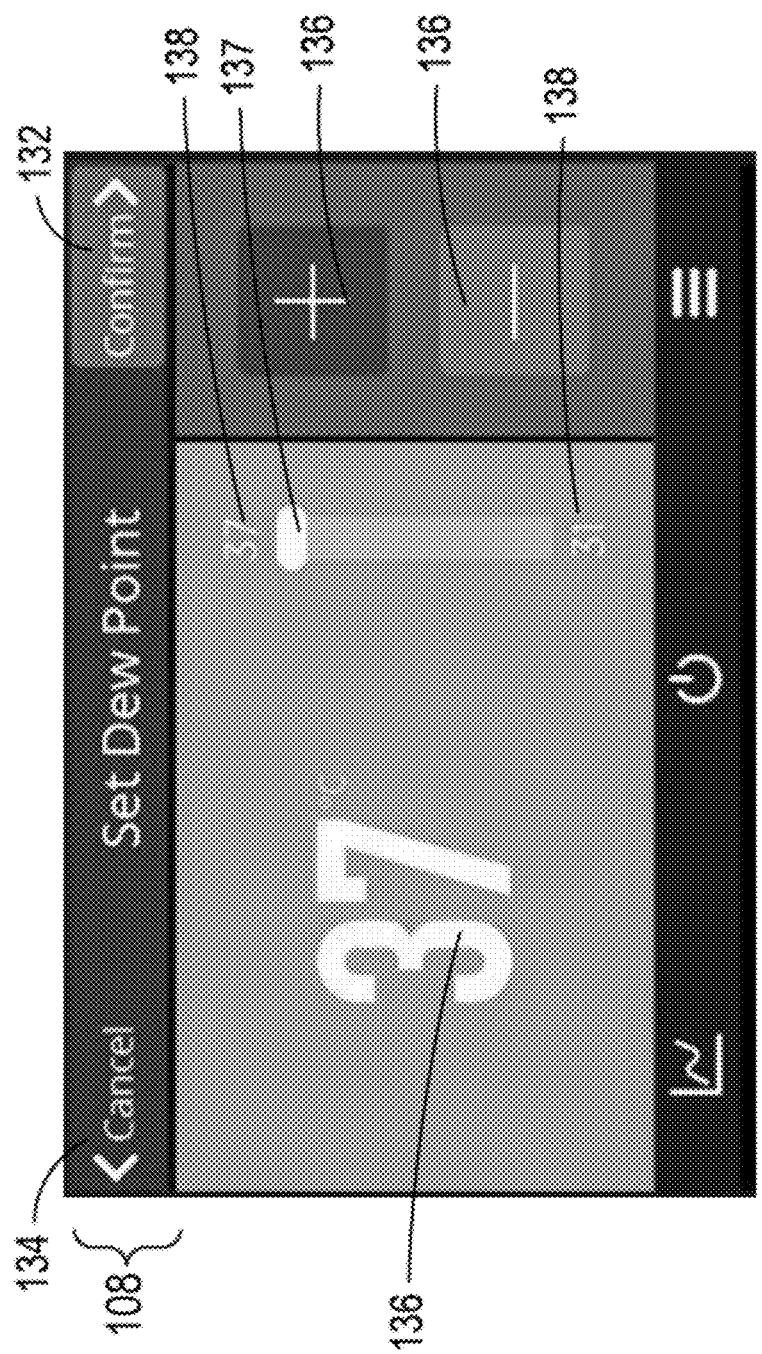
Figure 5F:
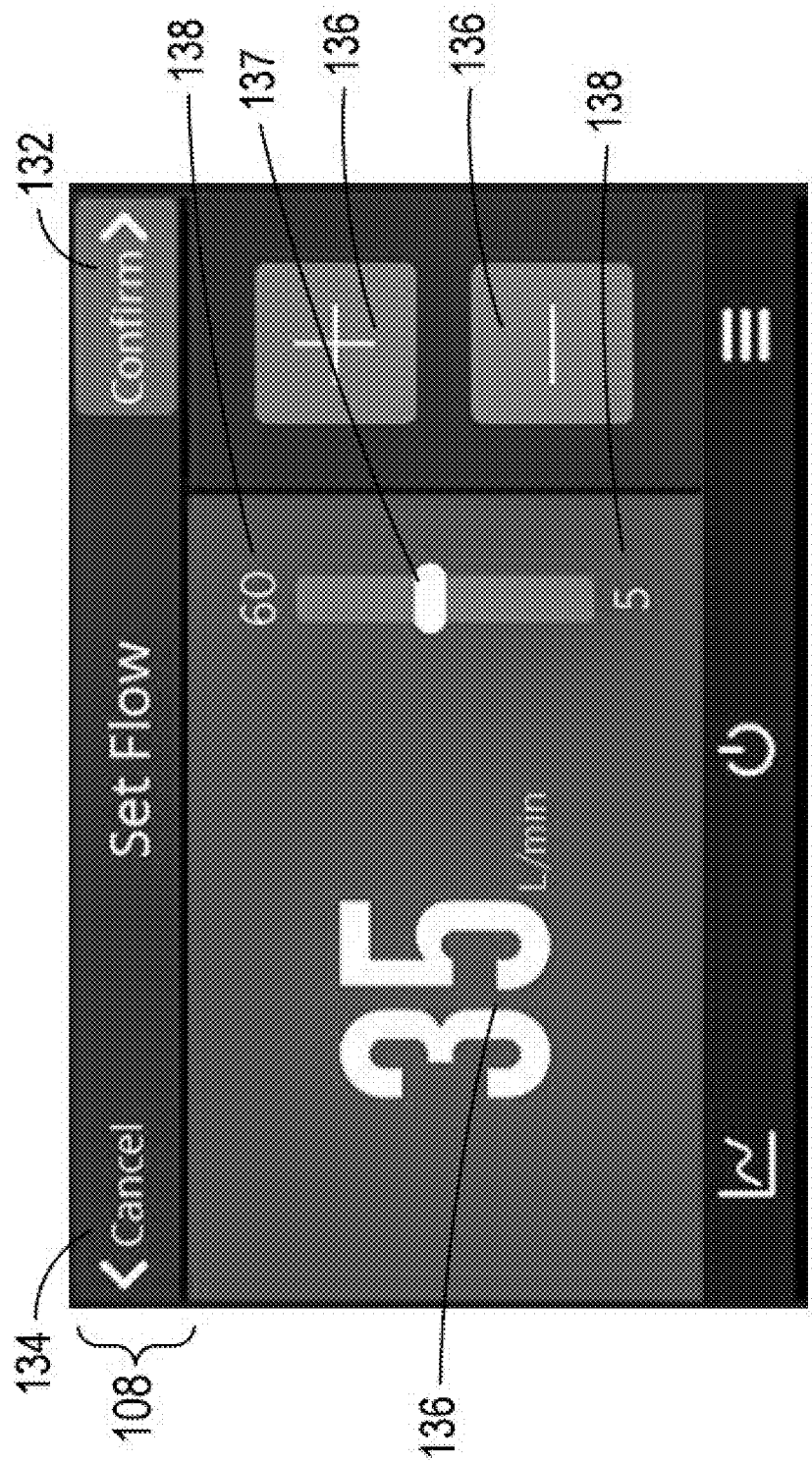

With reference to FIGS. 5A-5H, the user can alter the parameters of the parameter display elements 120 (also referred to as the operational values of the parameters) by selecting the parameter elements, such as by touching the element on a touch screen. The parameters may also be able to be modified through the settings. When a parameter is selected, the top portion 108 can be altered to provide information about the parameter that is being altered. The top portion can also include a confirm element 132 or a cancel element 134. The parameter alteration screen can allow for the user to set the operational value of the parameter for the flow therapy apparatus. The graphical user interface 100 can display input elements 136 configured to provide for the user to manipulate the parameter. For example the parameter may be increased or decreased. The inputs elements allow for the user to easily decrease or increase the value of the parameter. The graphical user interface may also include a range 138 or values indicative of a range of the operational limits of the parameter, such as illustrated in FIGS. 5A-5C. In some configurations, such as illustrated in FIGS. 5E-5F, the range can be illustrated by a bar extending between the upper and lower limit, with an icon 137 on the bar indicating where the current value is in relation to the limits.

Once an input is received from the user and confirmed, the lower portion 116 can provide a notification that the change to is being carried out by the flow therapy apparatus, such as indicated in FIG. 5D. The parameter display element 120 of the altered parameter can provide a visual indicator(s) that it is changing, such as flashing between a first and second brightness, changing the colour, changing the shade, or making another visual change to a display characteristic of the parameter display element. For example, the first brightness could be the normal level, with the second brightness being dimmer or brighter than the first brightness.

Figure 5G:

The FiO2 interface can include input controls 136 to modify the target FiO2, such as illustrated in FIGS. 5C and 5G. Once the FiO2 target has been chosen, the user can confirm this value, and the device will begin adjusting the FiO2 to this level.

Additionally, or alternatively, when a pulse oximeter is connected to the flow therapy apparatus or the flow therapy apparatus and the patient, the FiO2 interface can include an input 140 for initiating automatic closed loop control of the FiO2 value to maintain a target SpO2. This automatic mode input 140 may be unavailable if the SpO2 signal is too weak. The automatic mode input 140 may be unavailable based on other conditions, such as, the SpO2 measurement is too low, the flow is too low, flow restrictions, general fault conditions (e.g., water out, tube disconnect, etc.), and/or other conditions that would prevent the flow therapy apparatus from executing the automatic mode input. When the automatic mode is unavailable, the option may be completely removed from the graphical user interface, such as illustrated in FIG. 5G. Additionally, the lower display portion may display an indication of why the automatic mode is unavailable.

The FiO2 graphical user interface may include high and low buttons 139 (such as illustrated in FIG. 5G) that can be used to indicate whether a high pressure or low pressure oxygen source is connected to the flow therapy apparatus. A high pressure oxygen source is fed through the oxygen control valve, which the device can control in order to titrate the FiO2 to the desired level. A low pressure oxygen source is fed through a low pressure oxygen inlet, and the flow rate of this oxygen is not controlled by the device.

Figure 5H:

If the user selects low pressure, the screen illustrated in FIG. 5H can be displayed and the user is instructed to titrate the oxygen concentration using a flow rotameter. Automatic mode would also unavailable if a low pressure source is connected.

Figure 6A:
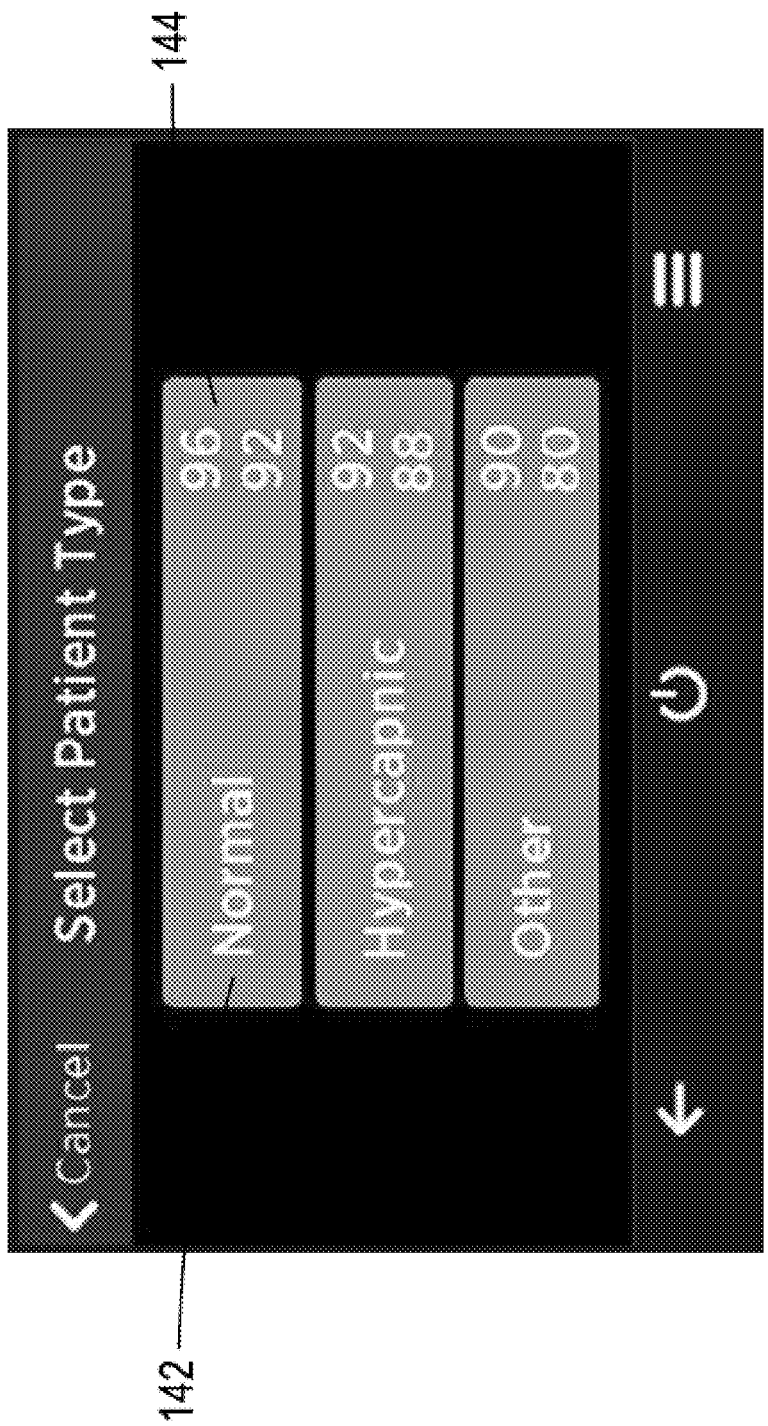
FIGS. 6A-6G illustrate graphical user interfaces of a flow therapy apparatus associated with an automatic mode of operation of the flow therapy apparatus.
Figure 6B:
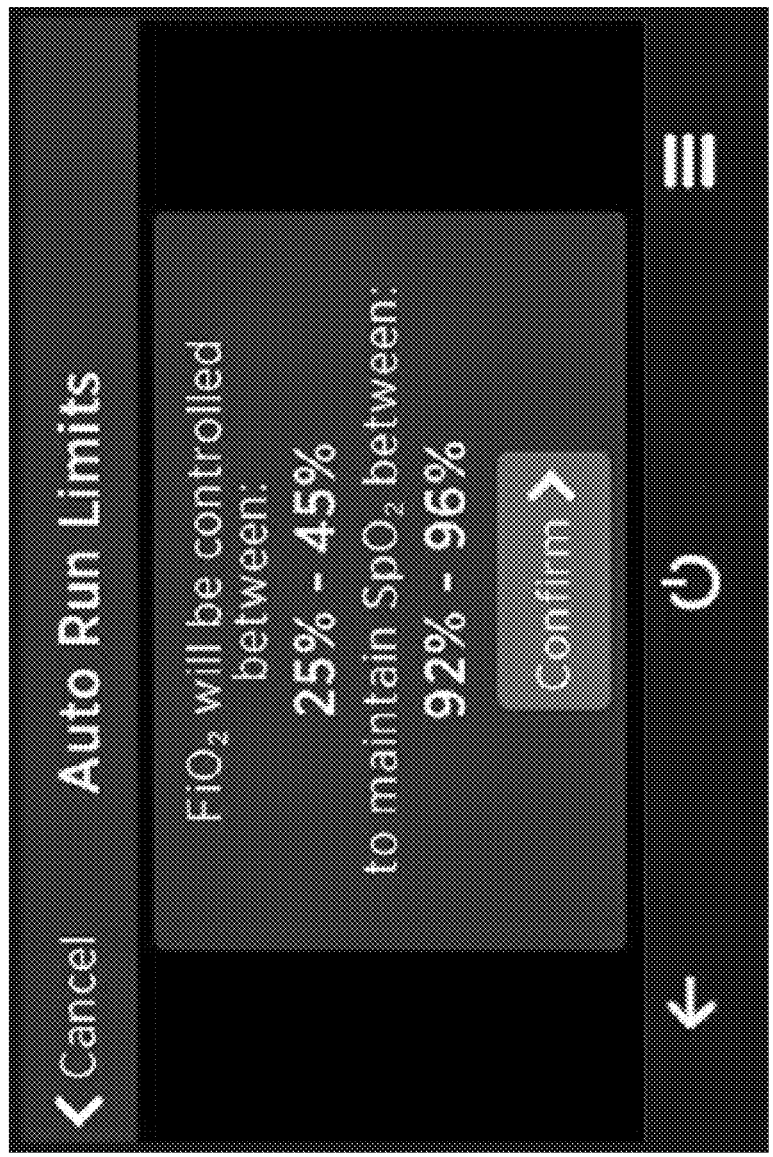
Figure 6C:
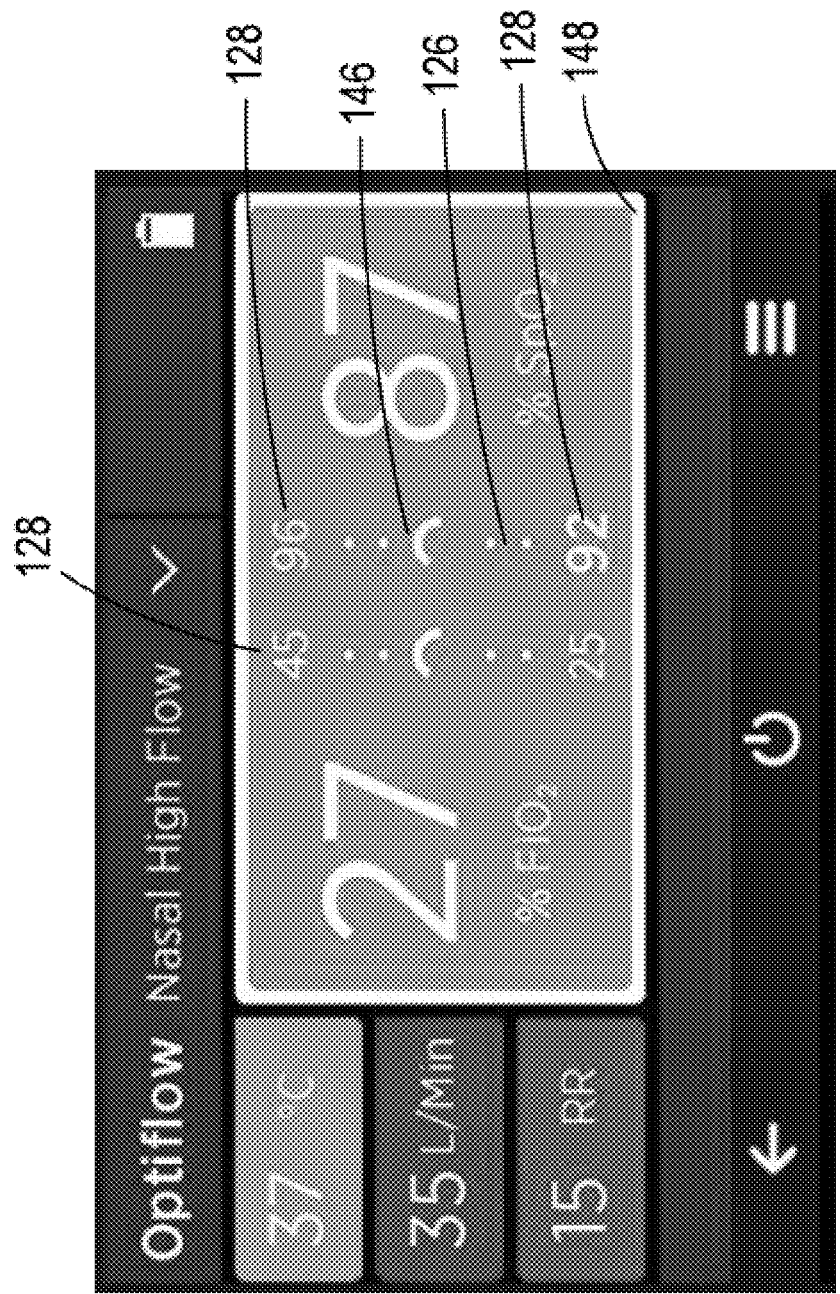
Figure 6D:

With reference to FIGS. 6C and 6D, the display for certain values may include a scale or range 126 showing limits 128 of the current range of the parameter, such as an acceptable range of SpO2 values for the patient. A value indicator 130 may indicate the value of the parameter on the scale 126 relative to the parameter limits 128. In some configurations, the value indicator may provide an indication of a trend of the parameter being measured. For example, the indication 130 may be a neutral icon (e.g., a circle) or a directional icon, such as an upward or downward facing arrow, which indicates whether the parameter value is rising or falling. The indication may transition between different types of icons based on the circumstances. The limits 128 may be selected based on specific limits associated with a patient. For example, with SpO2, the limits may be determined based on a healthy range for the patient. Additionally, the flow therapy apparatus may be configured to provide a visual indication to indicate that the element is outside of the acceptable limits, such as a change in colour of the limit value 128 and/or the indicator 130, the parameter display element may provide a visual effect (e.g., flash), and/or provide another indication. For example, in FIGS. 6C and 6D, the indicator 130 and the number indicating the lower limit of the scale changed colour in order to indicate that the value is outside of the acceptable range. The parameter value 122 may also change colour to indicate that the value is outside of the acceptable range.

Figure 6E:
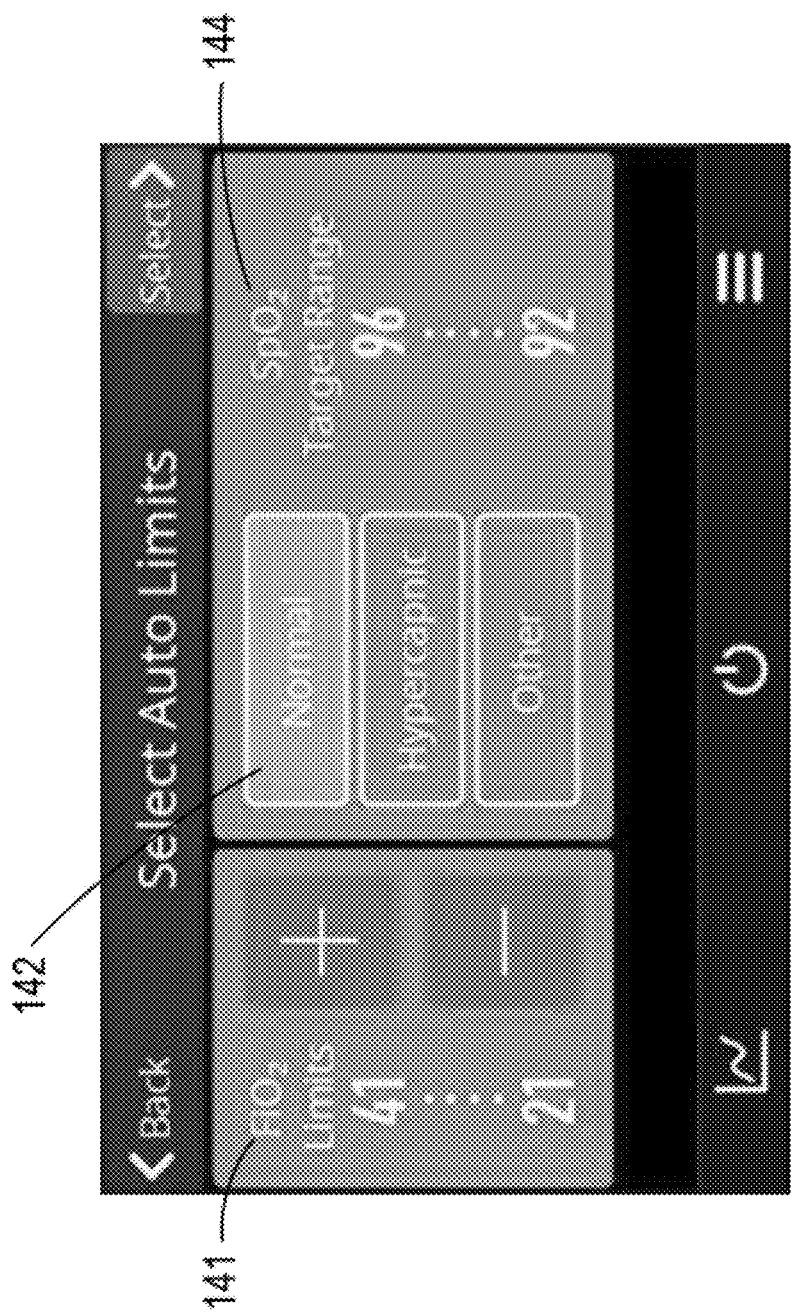

With reference to FIGS. 6A-6D, after the user selects automatic mode, such as by selecting the automatic mode input 140 in the FiO2 configuration interface screen, the graphical user interface 100 may display a subsequent screen (such as illustrated in FIG. 6A or 6E) where the user is prompted to input the type of patient. The graphical user interface includes a plurality of inputs 142 identifying types of patients, such as, normal, hypercapnic, other, or any type of patient. Patient type could include one or more parameters, such as patient condition, weight, height, age and/or gender. When selecting the SpO2 limits, the selectable options could be labelled without referring to patient type. For example, the options could be labelled with the SpO2 range, or as number (e.g., 1, 2, 3, etc.). Additionally, or alternatively, the options could be labelled high, medium, or low.

The patient type can determine the control limits for the SpO2. Corresponding control limits 144 for the patient type may be displayed beside each type of patient. Additionally, or alternatively, the patient type could influence one or more parameters of the control, particularly the default control algorithm that would be used in situations where patient characterisation fails, such as when the flow therapy apparatus fails to generate a patient specific model.

With reference to FIG. 6B, the graphical user interface can provide defined limits of operation of FiO2 of the flow therapy apparatus and the SpO2 of the patient. The user can be prompted to confirm the control limits for the patient. The control limits for FiO2 can be a percentage range from a starting point, such as 10% above and below the starting point. The limits may be further limited by physical limits of the flow therapy apparatus, such as a minimum of 21% FiO2. Alternatively, the user could be prompted to input selected limits for FiO2.

FIG. 6E illustrates a configuration of a screen that allows the user to adjust the FiO2 control range and the SpO2 target range on the same screen. The left portion of the screen displays the FiO2 control range beside plus and minus inputs. The plus and minus inputs can be used to adjust the FiO2 control range 141. The FiO2 limits can be controlled simultaneously, such that the upper and lower limits change at the same time as the user presses the plus or minus inputs. In certain situations, the FiO2 control range can be truncated by the physical limitations of the system, such as a maximum or minimum FiO2 that the system can deliver. In these situations, pressing the plus or minus input may result in only one of the upper and lower limits changing. In some configurations, the upper and lower limits can be decoupled and changed individually.

Figure 6F:
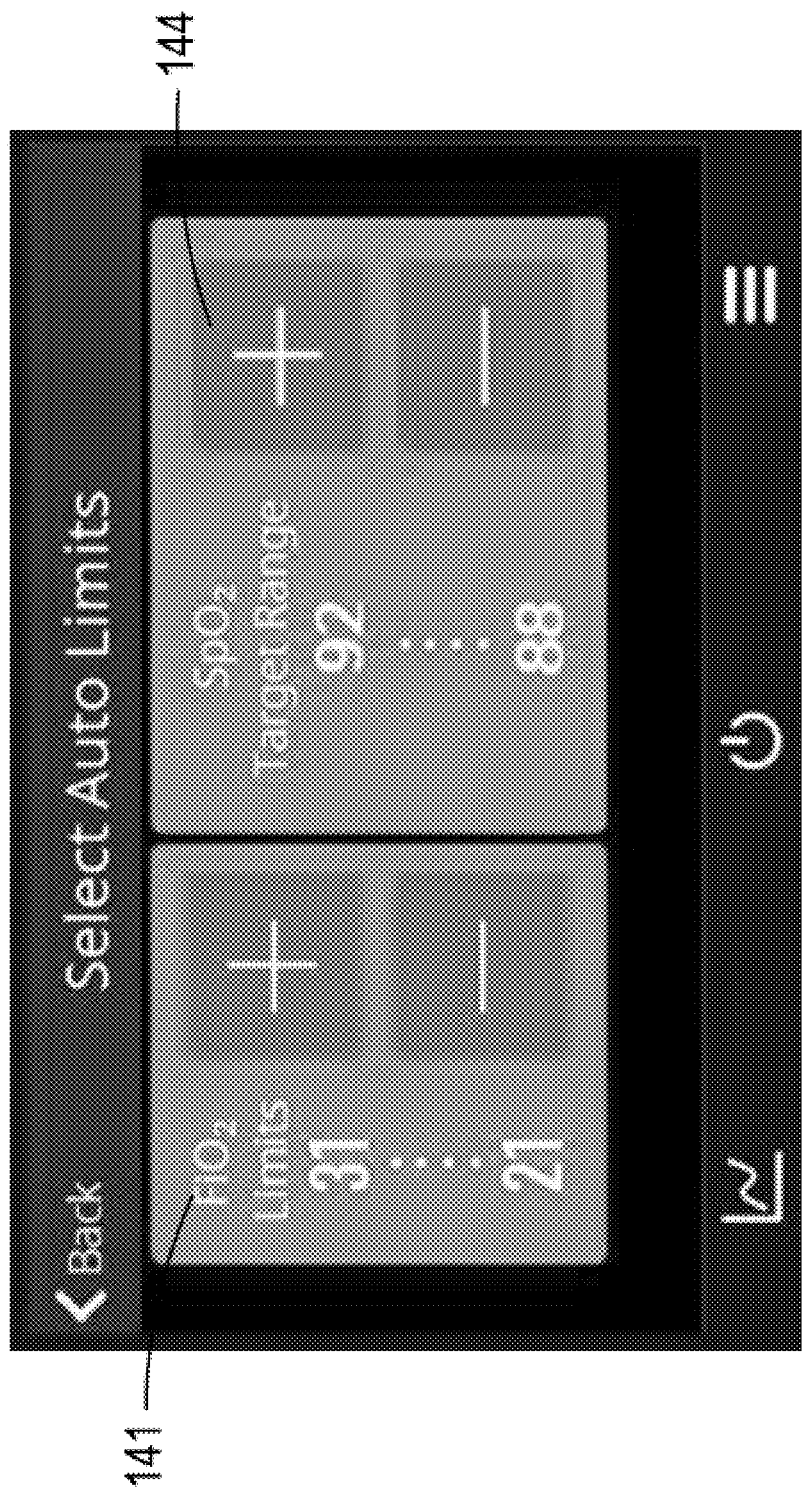
Figure 6G:
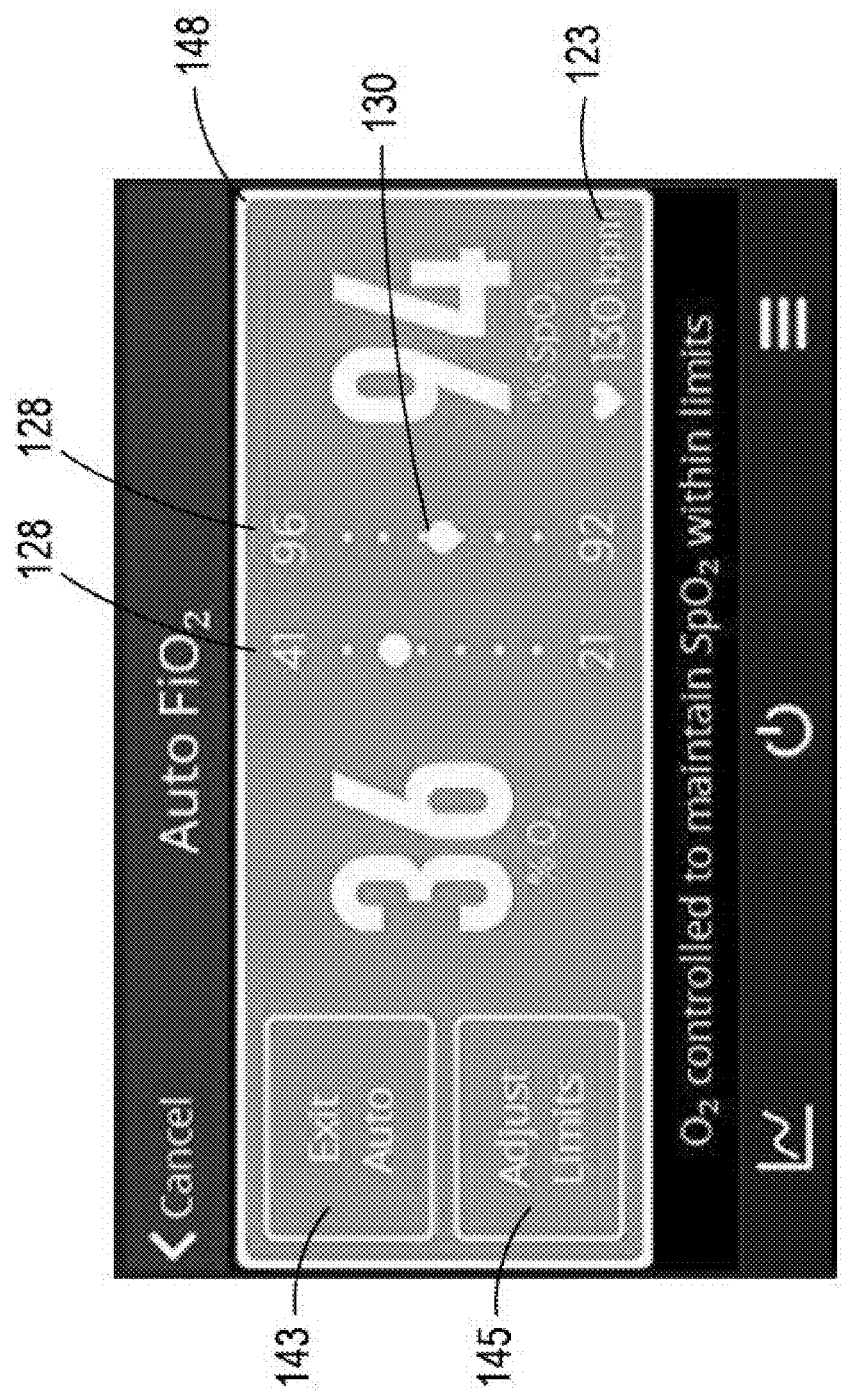

The right side of the screen is used to display the SpO2 target range beside various patient type inputs 142. When a user presses on one of these inputs 142, the selected patient type is highlighted, and the corresponding SpO2 control range 144 can be displayed. FIG. 6F illustrates a configuration where the user can cycle through possible SpO2 target ranges using the plus and minus inputs.

Selecting the input could involve changing the colour, shade, or brightness of the input. Additionally, or alternatively, selecting the input could involve adding one or more visual indicators, such as arrows, which indicate the patient type that has been selected.

The SpO2 target range could be displayed by showing the upper and lower limits of the target range, thereby indicating to the user the range in which the device will attempt to maintain the SpO2 within. Additionally, or alternatively, the SpO2 target range display could include a target value. This could indicate to the user what the target SpO2 value is within the SpO2 target range.

By having both the FiO2 control range and SpO2 target range displayed on the same screen, the user is able to adjust both ranges while being able to see both ranges. This allows a user, such as a clinician, to more easily decide the FiO2 control range based on the SpO2 target range. If the FiO2 control range and the SpO2 target range were set on different screens, then the user may need to swap back and forth between the two screens in order to make this determination.

[0145] After the user confirms, the flow therapy apparatus can enter the learning phase, feed forward phase, or another type of configuration phase prior to initiation of automatic mode. During the learning phase, the measured FiO2 and SpO2 values can be displayed. The device could have additional features to indicate that it is in the learning phase or automatic mode configuration.

The set value of FiO2 can be used for the step increase in FiO2 during the subsequent learning phase. Additionally, this value can be used for defining the FiO2 control limits. The user could additionally be prompted to input a step increase for the learning phase, although the selected FiO2 from the previous stage can be used by the flow therapy apparatus.

Additionally, or alternatively, the device could have the limits for FiO2 128 and/or limits for the SpO2 128 displayed next to the value of each parameter. An indicator 146, such as a spinning disc, could appear in the middle of each range, implying that the limits do not apply yet due to being in a learning phase or configuration phase.

Additionally, or alternatively, the parameter display elements 120 for FiO2 and SpO2 could be connected and/or have a linking indicator 148, such as a border around them, to indicate that the values are linked due to being in automatic control mode. The linking indicator can also modify the shape of the parameter display elements 120 in order to provide a visual indication to a user that parameters are no longer separate. For example, in FIGS. 6C, 6D, and 6G, the gap has been removed between the FiO2 and SpO2 parameter display elements. Additionally, the linking indicator 148 is a border that encapsulates both elements. Additionally, in the screen of FIG. 6G, the user is presented with two further options. One is to exit auto input 143, which would return the device to manual mode. The other is to adjust limits input 145, which allows the user to return to the previous closed loop control initiation screen, in which the user can adjust the FiO2 control range and the SpO2 target range. This screen may be configured to appear when the user presses the FiO2 parameter display element.

Once the learning phase or configuration phase is finished, an indicator 130 will display the position of the current measurements within their control limits. The indicators 130 provide an indication of how close each target each value is to its respective limits. If the SpO2 was too high or too low the indicator 130 would serve to show that something may be wrong with the patient and alert the patient or a caregiver that attention is required. Additionally, if the indicator for FiO2 was too high or too low on the range 126 (such as near the upper or lower limits) it could help to indicate that the FiO2 is straying far from the original set point or the centre of the control range in order to maintain the therapy. Having the indicators next to each other additionally allows for visual comparisons of the two values. If both were at the same level then there may be no need for concern with respect to the patient response, as if the FiO2 was low then it would be less worrying if the SpO2 was also low, as the low FiO2 would be attributed to the low SpO2 reading. However, if the FiO2 was significantly higher than the SpO2, then it could imply that the flow therapy apparatus is supplying a much higher than intended FiO2 in order to try to achieve a target SpO2 and the patient is not responding.

The control system of the flow therapy apparatus can attempt to alter the FiO2 within its control limits to try to maintain the SpO2 at the centre of its target range. However, the flow therapy apparatus can be configured so that it will not change the target FiO2 to a value outside of its control range, even if the flow therapy apparatus is not able to maintain the SpO2 with the control limits.

FIGS. 7A-7C illustrate interfaces associated with an alarm. The alarm interface can indicate that the flow therapy apparatus is no longer operating in automatic mode. If the flow therapy apparatus is unable to maintain the SpO2 within the target range using allowable FiO2 inputs. The flow therapy apparatus can alarm and revert to manual mode. The top portion 108 can display the reason for the alarm (e.g., SpO2 under limit). The flow therapy apparatus can trigger an alarm and include a user input control 150 that requires a user to acknowledge that the flow therapy apparatus has reverted to manual mode. Additionally, the graphical user interface can include a display element portion 152 that displays one or more parameters associated with the alarm, such as FiO2 and SpO2. In some configurations, the interface may display one or more parameters that are not related to the alarm, but which may still provide useful information for the user. For example, FiO2, SpO2, pulse rate, and/or other values may be displayed when a water out alarm associated with the humidifier is triggered.

In some configurations, the alarm does not cause the flow therapy apparatus to automatically revert to manual mode. After an alarm is triggered, the user can use input control 150 to cause the flow therapy apparatus to revert to manual mode. Alternatively, the user can minimize the alarm using control 151 (illustrated in FIG. 7B) to continue operation of the flow therapy apparatus in automatic mode. Once minimized, the warning would be moved to the lower display portion. The lower display portion could additionally include an input 153 and/or a visual effect (e.g., flash yellow) to indicate the alarm has not been resolved. Pressing on the input 153 and/or the lower display portion can then bring up the full screen alarm again (FIG. 7B). This can be advantageous to allow the user to attempt to resolve the fault without having to exit and re-enter automatic mode.

FIGS. 8A-8F provide examples of graphical user interfaces illustrating trend data. By selecting the menu button 106 or the trend button 103, a trends display can be accessed. The trends menu can have one or more parameters that can be viewed, such as FiO2, SpO2, flow rate, and respiratory rate. Two or more trends can be displayed in the same screen, such as FiO2 and SpO2. Having multiple parameters on the same screen may be useful in determining correlations between the parameters, such as FiO2 and SpO2, which can help assess a patient's condition.

The y-axis for each variable could automatically adjust to the range of the data set. For example, in FIG. 8A, the FiO2 above is shown on a scale between 20% and 40%. However, if the FiO2 went above this scale, the graphical user interface could adjust to a new scale, such as 20% to 60% to allow for the data to be shown. The x-axis can be a function of time. The scale can be any defined timeframe (e.g., 45 minutes). In the illustrated display the most recent data is on the far right, with the graph shifting left as new data is brought in. The x-axis may be configured to change to include all data from a session.

Figure 8A:
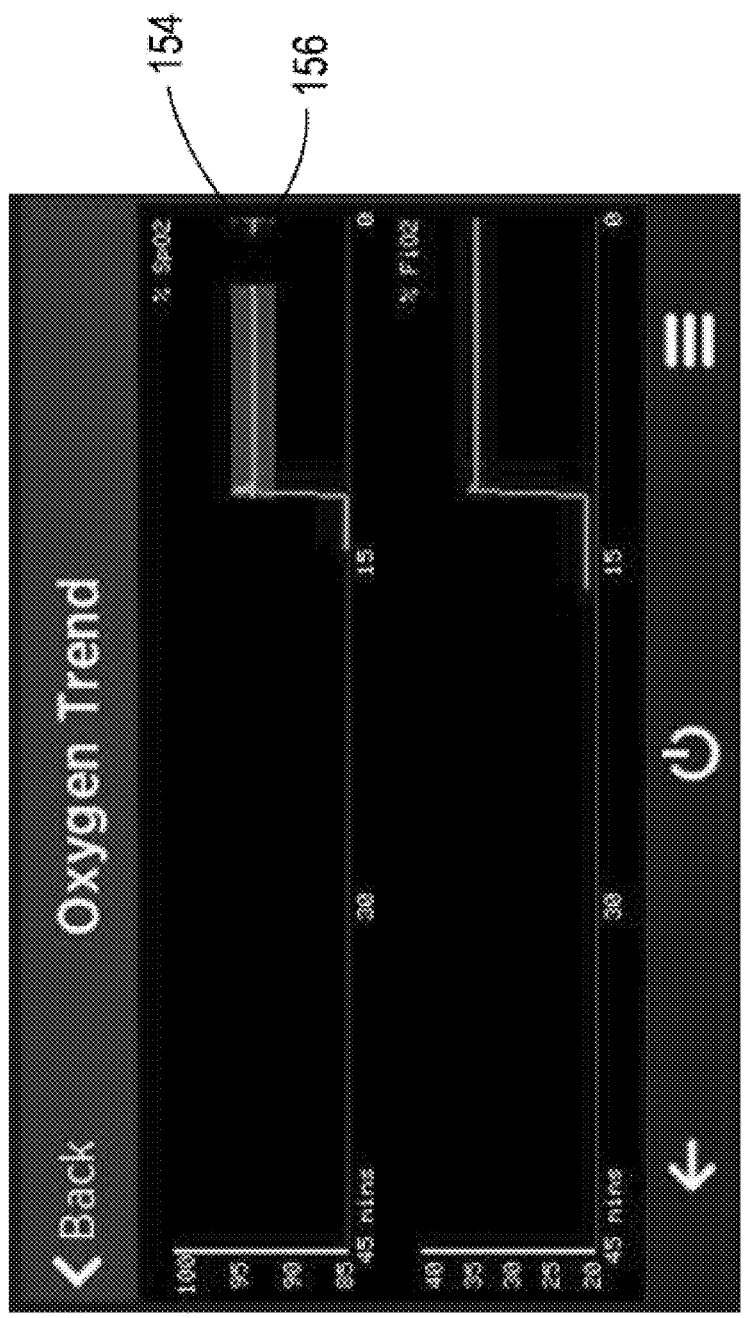
FIGS. 8A-8F illustrate graphical user interfaces of a flow therapy apparatus illustrating trend data.
Figure 8B:
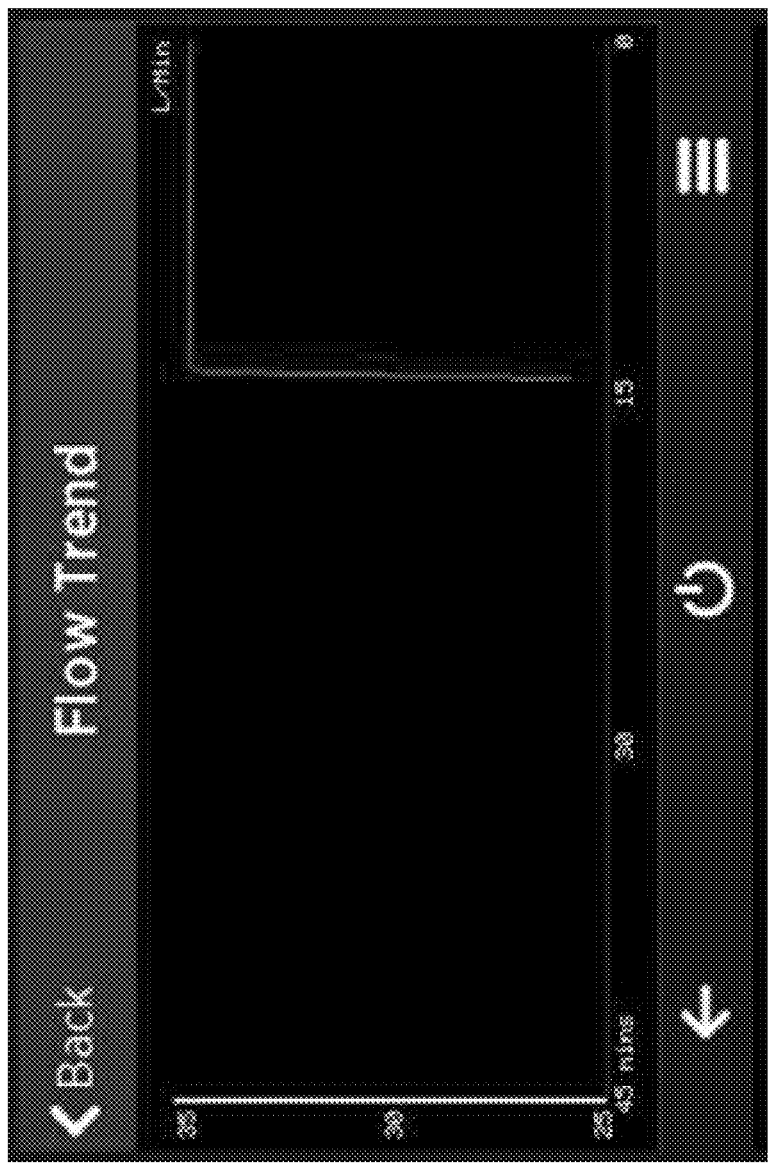
Figure 8C:
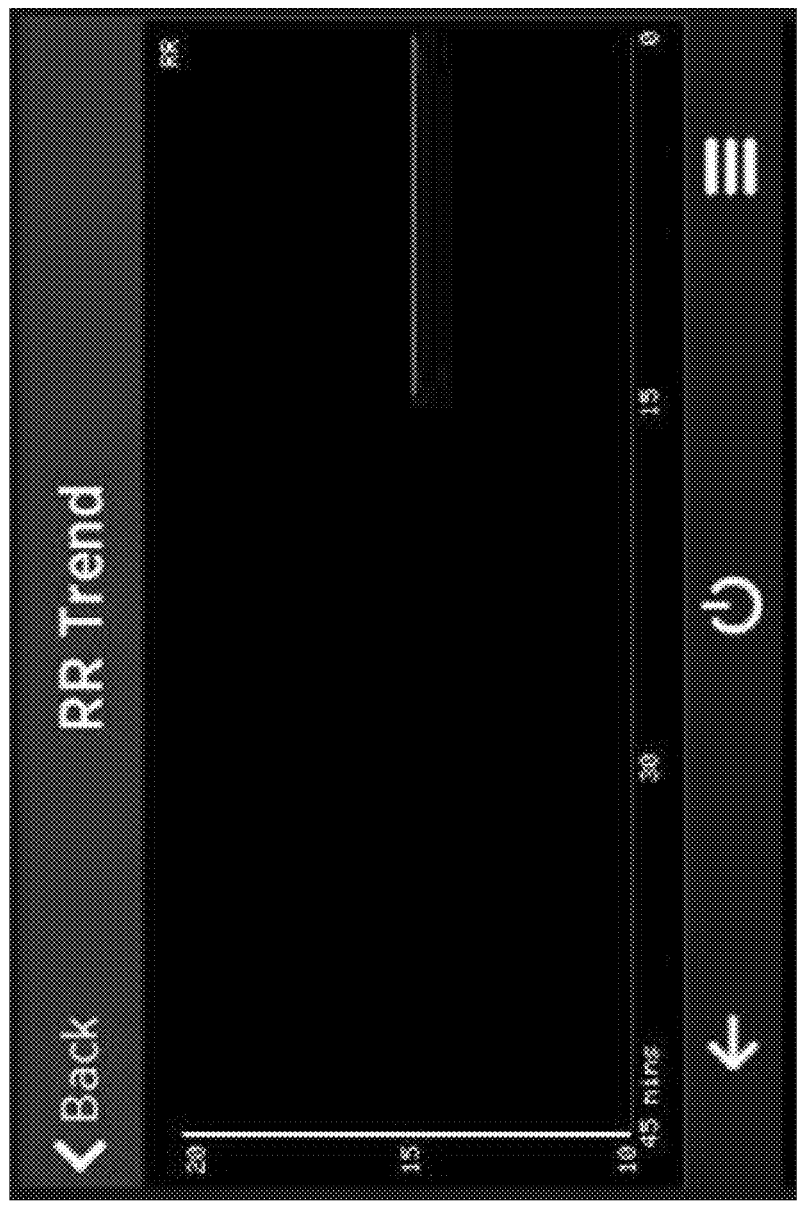
Figure 8D:
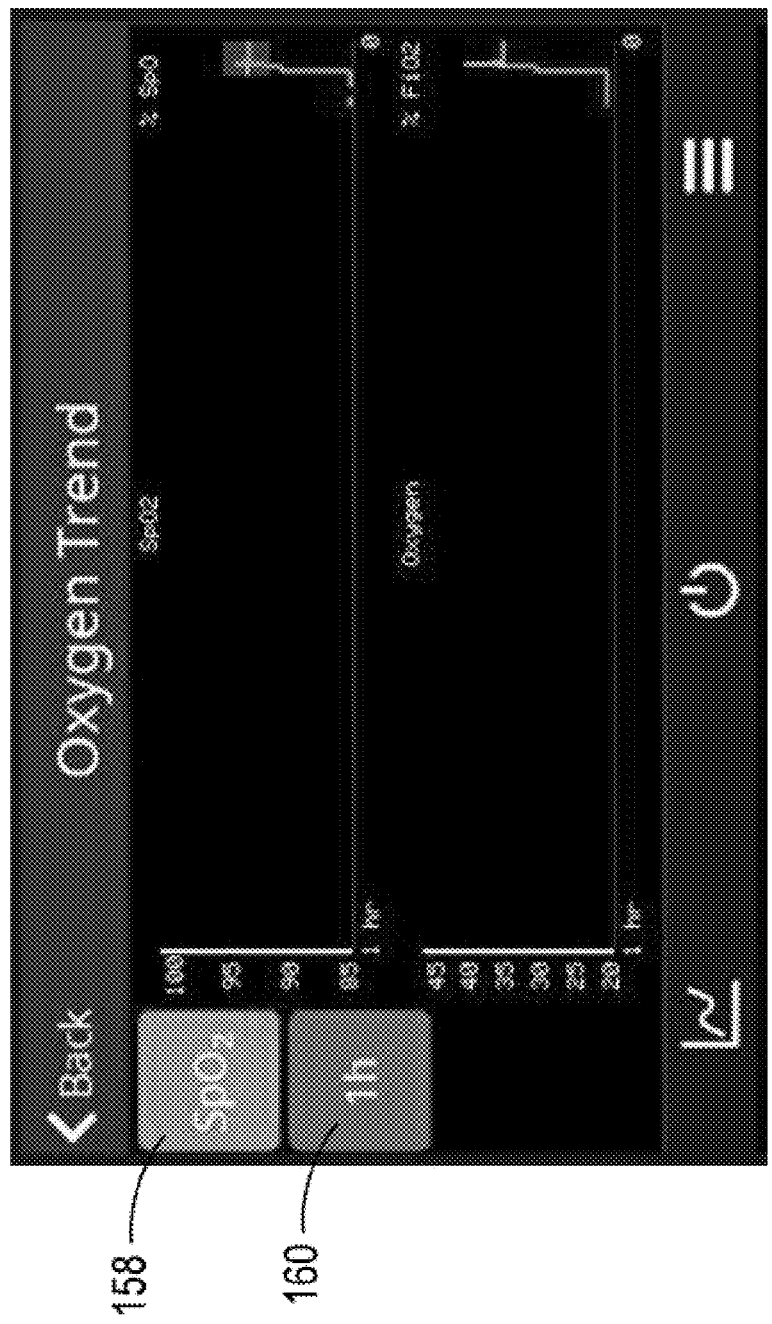
Figure 8E:
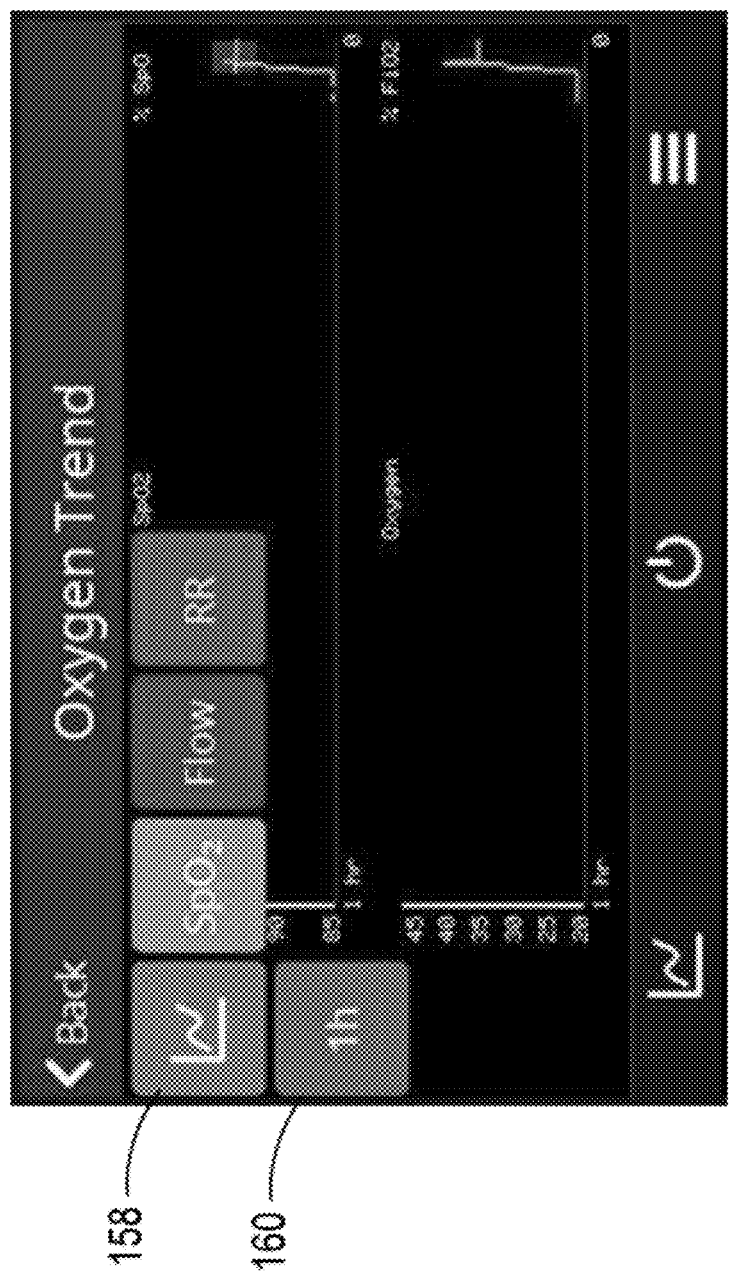
Figure 8F:
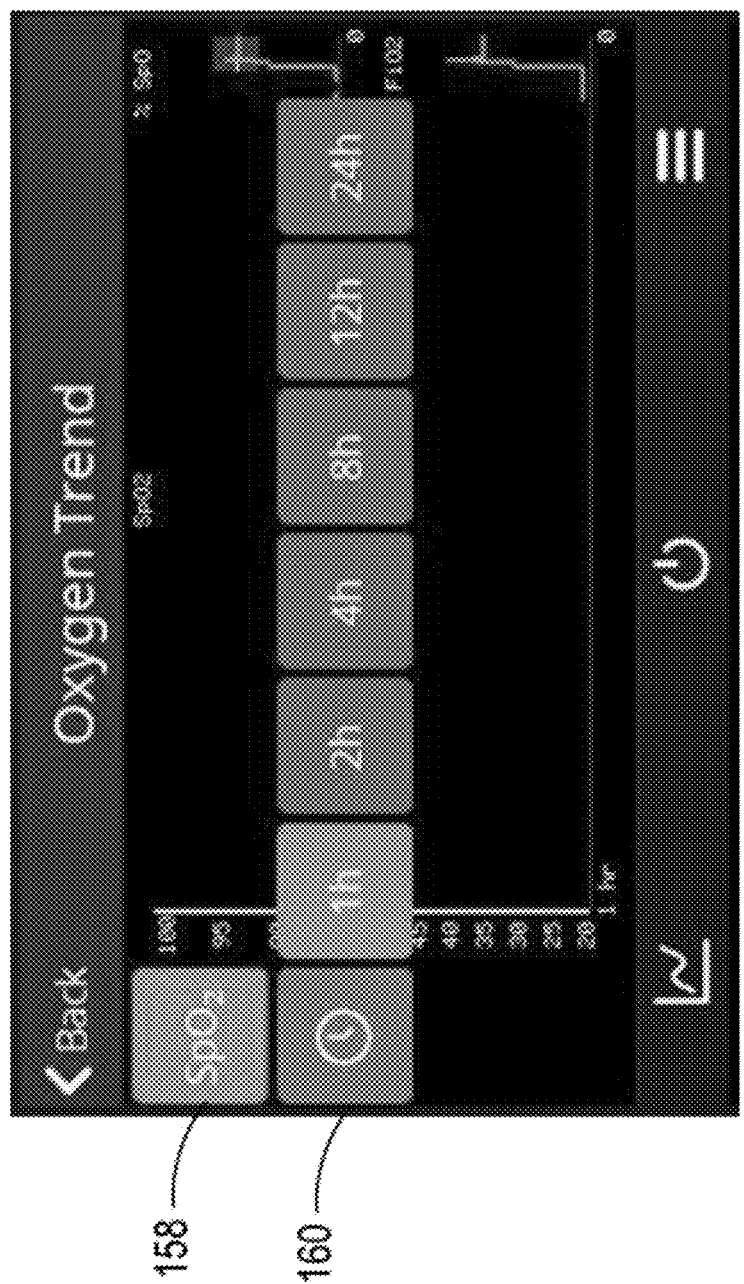

FIGS. 8D-8F illustrate a trend graph configuration that includes two inputs for manipulating the display of data on the trend graphs. These inputs indicate the timescale of the trend 160, and the parameter being displayed 158. When the parameter input 158 is pressed, the flow therapy apparatus displays a list of parameters for which trend data is available, such as SpO2, FiO2, flow rate, and respiratory rate. In some configurations, multiple parameters can be displayed simultaneously, such as FiO2 and SpO2.

The timescale input 160, when selected, provides a list of timescale options. The currently selected timescale can be highlighted. The timescale options include may include any defined times, such as 1 hour, 2 hours, 4 hours, 8 hours, 12 hours, 24 hours, or any other defined time scale. The timescale selected controls the window of time for which trend data is displayed. For example, selecting 1 hour will cause the trend screen to include data from the last hour. A user may want to select a longer timescale when the user wants to view how a parameter has changed over a longer period of time. Alternatively, the user may want to select a shorter timescale when only the more recent data is required, such as when the therapy has only recently begun. Reducing the timescale can allow for a more detailed view of said data, as this data for this time period can be stretched to fit the whole graph.

Trend data may also be available for further parameters and combinations of parameters, specifically those of clinical significance. For example, a measure of the patient's oxygen efficiency could be calculated by the device, with this data then being displayed as a trend over time. Oxygen efficiency would be based on the relationship between the patient's oxygen saturation and the oxygen concentration of the gas being delivered. For example, the oxygen efficiency could be calculated as SpO2 divided by the FiO2. Additionally, or alternatively, the device could display a trend of the SpO2 divided by the FiO2, then further divided by the patient's respiratory rate.

A trend graph can include a limit area 154 (e.g., a shaded area or top/bottom lines) indicating the control limits of the parameter (can also be referred to as operational thresholds), such as SpO2 control limits. The limit area can be visually distinct from the background and other display elements of the trend graph. The limits area may vary along the x axis. For example, the FiO2 graph could display a set of limits for a section of the x axis that represents a time period where the automatic mode was used, then no limits for a period of manual mode, and then new different limits for a subsequent period where auto mode with different FiO2 limits was used. The trend graph may have gaps for time periods where no data was available. For example, SpO2 may have gaps on its trend to indicate periods where signal quality of the SpO2 data was too low or it was unavailable. Additionally, or alternatively, the graph could have a line to indicate a target value for the parameter, such as a target SpO2.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The terms "approximately," "about," and "substantially" as used herein represent an amount close to the stated amount that still performs a desired function or achieves a desired result. For example, in some embodiments, as the context may permit, the terms "approximately", "about", and "substantially" may refer to an amount that is within less than or equal to 10% of, within less than or equal to 5% of, and within less than or equal to 1% of the stated amount.

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Depending on the embodiment, certain acts, events, or functions of any of the algorithms, methods, or processes described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

The invention claimed is:

1. A breathing assistance apparatus comprising:
    a housing;
    a display; and
    one or more processors configured with computer readable instructions to:
        generate a graphical user interface on the display, the graphical user interface comprising:
            a parameter display section comprising a first plurality of parameter display elements, each parameter display element associated with a parameter of the breathing assistance apparatus;
        receive a request to configure the breathing assistance apparatus in an automatic mode;
        generate a configuration graphical user interface displaying at least one patient type for configuring the automatic mode, wherein the at least one patient type is associated with a first parameter;
        receive an indication of a selection of a first patient type;
        determine control limits for the first parameter of the breathing assistance apparatus based on the first patient type; and
    operate the breathing assistance apparatus in the automatic mode using the control limits for the first parameter of the breathing assistance apparatus, wherein at least in the automatic mode the breathing assistance apparatus delivers high-flow therapy via a non-sealed patient interface comprising at least one nasal prong.

2. The breathing apparatus of claim 1, wherein the first parameter is SpO2, and the control limits are for the SpO2.

3. The breathing apparatus of claim 2, wherein the at least one patient type identifies a plurality of types of patients.

4. The breathing apparatus of claim 3, wherein the plurality of patient types include at least one of patient condition, patient weight, patient height, patient age, or patient gender.

5. The breathing apparatus of claim 4, wherein the first patient type is a normal patient condition.

6. The breathing apparatus of claim 5, wherein the SpO2 control limits for a normal type of patient are 92% SpO2 and 96% SpO2.

7. The breathing apparatus of claim 6, wherein a target SpO2 value is identified within the SpO2 control limits.

8. The breathing apparatus of claim 4, wherein the first patient type is a hypercapnic patient condition.

9. The breathing apparatus of claim 8, wherein the SpO2 control limits for a hypercapnic type of patient are 88% SpO2 and 92% SpO2.

10. The breathing apparatus of claim 9, wherein a target SpO2 value is identified within the SpO2 control limits.

11. The breathing apparatus of claim 3, wherein control limits associated with the first parameter are configured to be displayed next to each type of patient.

12. The breathing apparatus of claim 2, wherein the at least one patient type comprise a plurality of patient types and each patient type is associated with an alphanumeric identifier.

13. The breathing apparatus of claim 2, wherein each alphanumeric identifier is associated with a set of defined control limits.

14. The breathing apparatus of claim 2, wherein the one or more processors are further configured to determine control limits associated with a second parameter.

15. The breathing apparatus of claim 14, wherein second parameter is FiO2.

16. The breathing apparatus of claim 15, wherein the FiO2 control limits are adjustable by a user.

17. The breathing apparatus of claim 15, wherein the FiO2 control limits comprise an upper control limit and a lower control limit, wherein the upper control limit and the lower control limit are configured to be simultaneously adjusted when the user adjusts an input associated with the FiO2 control limits.

18. The breathing apparatus of claim 15, wherein the FiO2 control limits are a percentage range from a defined starting value.

19. The breathing apparatus of claim 14, wherein the one or more processors are further configured to provide a linking indicator visually linking parameter display elements for the first parameter with parameter display elements for the second parameter during the automatic mode.

* * * * *